US006749427B1

(12) United States Patent
Bretscher et al.

(10) Patent No.: US 6,749,427 B1
(45) Date of Patent: Jun. 15, 2004

(54) DENTAL ARTICLES INCLUDING POST-FORMABLE MULTILAYER OPTICAL FILMS

(75) Inventors: Kathryn R. Bretscher, Minneapolis, MN (US); Sumita B. Mitra, St. Paul, MN (US); Olester Benson, Jr., Woodbury, MN (US); James M. Jonza, Woodbury, MN (US); William W. Merrill, White Bear Lake, MN (US); Andrew J. Ouderkirk, Woodbury, MN (US); Michael F. Weber, Shoreview, MN (US); Janis R. Gust, Minneapolis, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/127,137

(22) Filed: Jul. 31, 1998

(51) Int. Cl.[7] .............................. A61B 1/24; A61C 1/00; A61C 5/04
(52) U.S. Cl. ............................................. 433/30; 29/39
(58) Field of Search ................................ 433/29, 30, 31; 359/494, 497, 498, 500, 584

(56) References Cited

U.S. PATENT DOCUMENTS

| 1,345,718 A | * | 7/1920 | Underwood ................. 433/30 |
| 3,124,639 A | * | 3/1964 | Kahn |
| 3,464,601 A | * | 9/1969 | Christensen |
| 3,565,985 A | * | 2/1971 | Schrenk et al. |
| 3,594,457 A | * | 7/1971 | Wright ........................ 350/406 |
| 3,610,729 A | * | 10/1971 | Rogers ........................ 359/488 |
| 3,613,246 A | * | 10/1971 | Zdarsky ........................ 433/30 |
| 3,711,176 A | * | 1/1973 | Alfrey, Jr. et al. .............. 350/1 |
| 3,801,429 A | * | 4/1974 | Schrenk et al. ............. 161/181 |
| 3,829,199 A | * | 8/1974 | Brown ......................... 433/30 |
| 3,860,036 A | * | 1/1975 | Newman, Jr. ................ 138/45 |
| 4,080,476 A | * | 3/1978 | Laskey ........................ 428/413 |
| 4,162,343 A | * | 7/1979 | Wilcox et al. .............. 428/212 |
| 4,446,305 A | * | 5/1984 | Rogers et al. .............. 528/348 |
| RE31,780 E | * | 12/1984 | Cooper et al. .............. 428/212 |
| 4,520,189 A | * | 5/1985 | Rogers et al. .............. 528/331 |
| 4,521,588 A | * | 6/1985 | Rogers et al. .............. 528/363 |
| 4,525,413 A | * | 6/1985 | Rogers et al. .............. 428/212 |
| 4,592,726 A | * | 6/1986 | Brilliant ....................... 433/31 |

(List continued on next page.)

FOREIGN PATENT DOCUMENTS

| EP | 0375161 | * | 6/1990 |
| WO | WO 95/17303 | * | 6/1995 |
| WO | WO 95/17691 | * | 6/1995 |
| WO | WO 95/17692 | * | 6/1995 |
| WO | WO 95/17699 | * | 6/1995 |
| WO | WO 95/27919 | * | 10/1995 |
| WO | WO 96/19347 | * | 6/1996 |
| WO | WO 97/01440 | * | 1/1997 |
| WO | WO 97/01774 | * | 1/1997 |
| WO | WO 97/32224 | * | 9/1997 |
| WO | WO 97/32226 | * | 9/1997 |

OTHER PUBLICATIONS

Schrenk et al., "Nanolayer polymeric optical films," *Tappi Journal*, 169–174 (1992).*

Primary Examiner—Nicholas D. Lucchesi
(74) Attorney, Agent, or Firm—James D. Christoff

(57) ABSTRACT

Dental articles including at least one optical surface formed of a multilayer optical film including layers of at least one strain-induced birefringent material are disclosed. The multilayer optical films included in the dental articles is preferably post-formed into desired non-planar shapes in manners that result in some deformation of the optical stack of the multilayer optical films. A variety of dental implements can be constructed with multilayer optical film including dental mirrors, light guides for use in connection with photo-curing dental materials, and matrix bands for use in molding photo-curing dental restoratives.

27 Claims, 14 Drawing Sheets

U.S. PATENT DOCUMENTS

| | | | | |
|---|---|---|---|---|
| 4,720,426 A | * | 1/1988 | Englert et al. | 428/344 |
| 4,937,134 A | * | 6/1990 | Schrenk et al. | 428/213 |
| 5,089,318 A | * | 2/1992 | Shetty et al. | 428/212 |
| 5,094,788 A | * | 3/1992 | Schrenk et al. | 264/171 |
| 5,094,793 A | * | 3/1992 | Schrenk et al. | 264/171 |
| 5,103,337 A | * | 4/1992 | Schrenk et al. | 359/359 |
| 5,122,905 A | * | 6/1992 | Wheatley et al. | 359/586 |
| 5,122,906 A | * | 6/1992 | Wheatley | 359/586 |
| 5,126,880 A | * | 6/1992 | Wheatley et al. | 359/587 |
| 5,147,204 A | * | 9/1992 | Patten et al. | 433/229 |
| 5,154,765 A | * | 10/1992 | Armanini | 106/401 |
| 5,188,760 A | * | 2/1993 | Hikmet et al. | 252/299.01 |
| 5,211,878 A | * | 5/1993 | Reiffenrath et al. | 252/299.63 |
| 5,211,997 A | * | 5/1993 | Patel et al. | 428/29 |
| 5,217,794 A | * | 6/1993 | Schrenk | 428/220 |
| 5,233,465 A | * | 8/1993 | Wheatley et al. | 359/359 |
| 5,235,443 A | * | 8/1993 | Barnik et al. | 359/37 |
| 5,262,894 A | * | 11/1993 | Wheatley et al. | 359/586 |
| 5,269,683 A | * | 12/1993 | Hickok et al. | 433/30 |
| 5,269,995 A | * | 12/1993 | Ramanathan et al. | 264/171 |
| 5,278,694 A | * | 1/1994 | Wheatley et al. | 359/359 |
| 5,294,657 A | * | 3/1994 | Melendy et al. | 524/270 |
| RE34,605 E | * | 5/1994 | Schrenk et al. | 359/359 |
| 5,316,703 A | * | 5/1994 | Schrenk | 264/1.3 |
| 5,319,478 A | * | 6/1994 | Fünfschilling et al. | 359/53 |
| 5,339,198 A | * | 8/1994 | Wheatley et al. | 359/359 |
| 5,348,470 A | * | 9/1994 | McGowan | 433/30 |
| 5,360,659 A | * | 11/1994 | Arends et al. | 428/216 |
| 5,389,324 A | * | 2/1995 | Lewis et al. | 264/171 |
| 5,440,393 A | * | 8/1995 | Wenz | 356/376 |
| 5,448,404 A | * | 9/1995 | Schrenk et al. | 359/584 |
| 5,486,935 A | * | 1/1996 | Kalmanash | 359/37 |
| 5,486,949 A | * | 1/1996 | Schrenk et al. | 359/498 |
| 5,540,978 A | * | 7/1996 | Schrenk | 428/212 |
| 5,552,927 A | * | 9/1996 | Wheatly et al. | 359/584 |
| 5,568,316 A | * | 10/1996 | Schrenk et al. | 359/584 |
| 5,612,820 A | * | 3/1997 | Schrenk et al. | 359/498 |
| 5,626,476 A | * | 5/1997 | Champagne | 433/226 |
| 5,629,055 A | * | 5/1997 | Revol et al. | 428/1 |
| 5,659,531 A | * | 8/1997 | Ono et al. | 359/494 |
| 5,684,633 A | * | 11/1997 | Lutz et al. | 359/588 |
| 5,686,979 A | * | 11/1997 | Weber et al. | 349/96 |
| 5,699,188 A | * | 12/1997 | Gilbert et al. | 359/584 |
| 5,721,603 A | * | 2/1998 | De Vaan et al. | 349/194 |
| 5,724,185 A | * | 3/1998 | Hickey et al. | 359/500 |
| 5,744,534 A | * | 4/1998 | Ishiharada et al. | 524/442 |
| 5,751,388 A | * | 5/1998 | Larson | 349/96 |
| 5,753,890 A | * | 5/1998 | Nevin | 433/30 |
| 5,767,935 A | * | 6/1998 | Ueda et al. | 349/112 |
| 5,770,306 A | * | 6/1998 | Suzuki et al. | 428/328 |
| 5,783,120 A | * | 7/1998 | Ouderkirk et al. | 264/1.34 |
| 5,793,456 A | * | 8/1998 | Broer et al. | 349/98 |
| 5,805,336 A | * | 9/1998 | Dalzell et al. | 359/494 |
| 5,808,794 A | * | 9/1998 | Weber et al. | 359/487 |
| 5,825,542 A | * | 10/1998 | Cobb, Jr. et al. | 359/487 |
| 5,825,543 A | * | 10/1998 | Ouderkirk et al. | 359/494 |
| 5,841,584 A | * | 11/1998 | Takatani et al. | 359/584 |
| 5,867,239 A | * | 2/1999 | Sahouani et al. | 349/117 |
| 5,867,329 A | * | 2/1999 | Justus et al. | 359/584 |
| 5,882,774 A | * | 3/1999 | Jonza et al. | 428/212 |

* cited by examiner

DENTAL ARTICLES INCLUDING POST-FORMABLE MULTILAYER OPTICAL FILMS

The present invention relates to the field of dental articles. More articularly, the present invention relates to dental articles including post-formable ultilayer optical films including at least one birefringent material.

BACKGROUND

The use and/or control of light energy is important in many dental procedures, particularly those in which photo-curing adhesives, sealants and dental restorative materials are used. Photo-curing materials preferably cure when exposed to light having a selected wavelength or wavelengths, typically in the visible spectrum.

Photo-curable dental materials are a convenience to the dentist because the curing process can be initiated when desired. For example, a dental filling may be placed in a tooth cavity in contact with a photo-curable dental adhesive and manipulated as needed until the dentist is satisfied that the filling is oriented in its proper position. A source of light including the selected wavelength or wavelengths is then activated to initiate polymerization of the adhesive and securely fix the filling in place. Even in those dental procedures in which photo-curing dental materials are not used, the delivery and control of light is important to allow dental personnel to view the procedures being performed.

Conventional methods of providing reflective optical surfaces in connection with dental articles typically include the use of metal or substrates coated with thin layers of metals. Forming the dental articles including reflective optical surfaces completely of metal is typically expensive and may also suffer from other disadvantages such as increased weight, etc. Metal-coated optical surfaces are typically plastic or other substrates coated with a reflective metallic layer by, e.g., vacuum, vapor or chemical deposition. These coatings suffer from a number of problems including chipping or flaking of the metallic coating, as well as corrosion of the metallic layer.

These problems are exacerbated in many dental applications because the dental articles, including the optical surfaces, that are used in multiple procedures must typically be sterilized between procedures. Sterilization subjects the articles to heat and humidity that can increased the rate of degradation of the optical surfaces. For those dental articles including optical surfaces that may only be metal-coated, the problems of degradation can be even more severe when subjected to sterilization. In many cases, the dental articles including metal-coated optical surfaces may be disposed of after a single use which can increase the cost of the procedures in which those dental articles are used.

When used in connection with photo-curing dental restoratives, another disadvantage of many of the optical surfaces of dental articles includes their inability to selectively reflect or transmit desired wavelengths of light. Many photo-curing dental materials are activated or cured by light in a relatively narrow range of wavelengths, typically in the visible spectrum. Known optical surfaces of dental articles, however, are typically opaque (i.e., they reflect and/or absorb incident light) or they are transmissive for the visible spectrum, thereby preventing or making it difficult to observe the photo-curing dental materials during use without delivering at least some light in the photo-curing wavelengths. As a result, the need to observe the working area can cause at least some photo-curing of the dental materials.

In addition to the above considerations, dental articles often include optical surfaces that are not planar in shape, i.e., the optical surfaces are in the shape of simple or complex curves. Examples include a dental mirror with an optical surface in the shape of a convex surface, a light guide used in connection with the delivery of photo-curing light that employs a curved reflective tube to deliver light from a source to a location within a patient's mouth, etc.

SUMMARY OF THE INVENTION

The present invention provides dental articles including at least one optical surface formed of a multilayer optical film including layers of at least one strain-induced birefringent material. The multilayer optical films included in the dental articles is preferably post-formed into desired non-planar shapes in manners that result in some deformation of the optical stack of the multilayer optical films.

The term "dental implements" as used in connection with the present invention includes devices having at least one optical surface that is designed for use in a dental procedure including, but not limited to: dental mirrors, light guides for use in connection with photo-curing dental materials, matrix bands for use in molding photo-curing dental restoratives, etc. As used in connection with the present invention, the term "dental articles" encompasses devices used in connection with dental procedures. As a result, dental articles includes dental implements designed for use within a patient's mouth, as well as devices designed to assist dental professionals in dental procedures such as dental operatory lights, room lighting covers, etc. Dental articles also include at least one optical surface. As used herein, the term "optical surface" means a surface that reflects, absorbs, and/or transmits light in a desired manner. In some situations, an optical surface may reflect light of some wavelengths and transmit light of other wavelengths, the optical surface may reflect substantially all incident light, or the optical surface may transmit substantially all incident light, etc.

Among the advantages of the present invention is the ability to improve visibility within a patient's mouth during dental procedures. By including the highly reflective multilayer optical films according to the present invention, the dental implements are capable of reflecting more of the available light, resulting in improved visibility for dental professionals. In addition, where light is used to photocure dental materials, the improved reflectivity of the multilayer optical films may reduce the curing time, thereby saving time for both the dental professional and the patient.

In one aspect, the present invention provides a dental article including at least one optical surface reflecting light of desired wavelengths, wherein the optical surface includes an optical stack having a plurality of layers, the layers including at least one birefringent polymer and at least one different polymer, wherein the optical stack includes first and second strain-induced index of refraction differentials, the first and second index of refraction differentials being located along first and second perpendicular in-plane axes, and further wherein the thickness of the optical stack varies over the optical surface. The dental articles can be dental implements, e.g., dental mirrors, dental light guides, matrix bands, etc.

In another aspect, the present invention provides a dental article including a lamp cavity having a first optical surface, the first optical surface reflecting light in a first set of desired wavelengths, the lamp cavity further including an opening; and a lens located over at least a portion of the opening in the lamp cavity, the lens having a second optical surface, wherein the second optical surface reflects light in a second set of desired wavelengths; wherein at least one of the first and second optical surfaces includes an optical stack including a plurality of layers, the layers including at least one birefringent polymer and at least one different polymer, wherein the optical stack includes first and second strain-induced index of refraction differentials, the first and second index of refraction differentials being located along first and second perpendicular in-plane axes, and further wherein the thickness of the optical stack varies over the optical surface.

These and other features and advantages of the present invention are discussed below.

BRIEF DESCRIPTION OF THE DRAWINGS

FIG. 11 is a perspective view of a dental mirror including post-formed multilayer optical film according to the present invention.

DETAILED DESCRIPTION OF ILLUSTRATIVE EMBODIMENTS OF THE INVENTION

Figure 1:
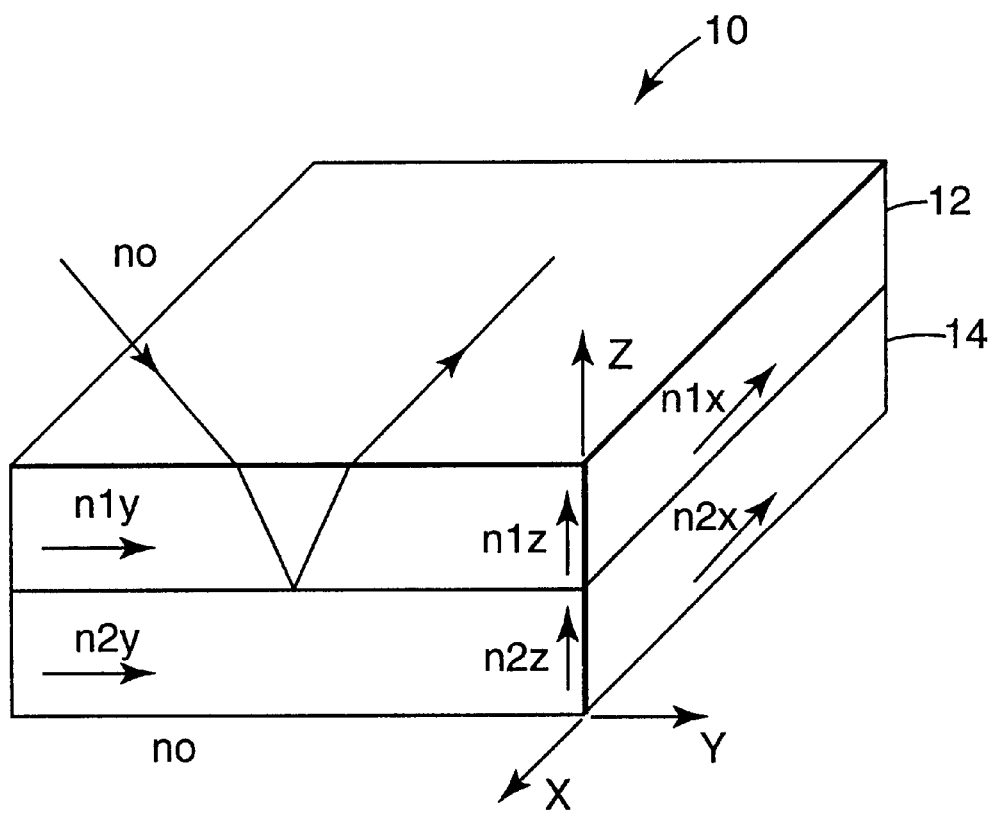
FIG. 1 is a schematic diagram of one multilayer optical film according to the present invention.

The present invention is directed at dental articles including at least one optical surface of a post-formed multilayer optical film including layers of at least one strain-induced birefringent material. The post-formed multilayer optical films used in dental articles according to the present invention are useful in that they can reflect or transmit desired wavelengths of light in desired manners to obtain desired results.

Optical films and methods of post-forming those films can be found in both U.S. patent application Ser. No. 09/126,917, titled POST-FORMABLE MULTILAYER OPTICAL FILMS AND METHODS OF FORMING and in U.S. patent application Ser. No. 09/127,314, titled POST-FORMING CONTINUOUS/DISPERSE PHASE OPTICAL BODIES, both filed on even date herewith.

By using multilayer optical films in the dental articles according to the present invention, the advantages of multilayer optical films, such as high reflectivity, selective transmission/reflection of light having desired wavelengths, light weight, etc., can be provided in dental articles. The selective transmission/reflection of light having desired wavelengths may be particularly advantageous when used in connection with photo-curing dental materials to control the delivery of the light in the photo-curing wavelength or wavelengths. Using multilayer optical films may be especially useful for UV absorbance and/or IR reflectance in dental applications.

Because the optical surfaces of many of the dental articles are non-planar, the ability to provide multilayer optical films for those optical surfaces requires some post-forming of the multilayer optical films from their generally planar film shape as manufactured. Post-forming of multilayer optical films presents problems because most, if not all, post-forming processes result in deformation of the film from its manufactured state. Those deformations can adversely affect the optical and mechanical properties of the multilayer optical film.

While the present invention is frequently described herein with reference to the visible region of the spectrum, various embodiments of the multilayer optical films used in dental articles according to the present invention can operate at different wavelengths (and thus frequencies) of electromagnetic radiation. For simplicity, the term "light" will be used herein to refer to any electromagnetic radiation (regardless of the wavelength/frequency of the electromagnetic radiation) capable of being reflected by the multilayer optical films of the present invention. For example, the multilayer optical films may be capable of reflecting very high, ultrahigh, microwave and millimeter wave frequencies of electromagnetic radiation. More preferably, the term "light" will refer to electromagnetic radiation including the ultraviolet through the infrared spectrum (including the visible spectrum). Even more preferably, "light" as used in connection with the present invention can be defined as electromagnetic radiation in the visible spectrum.

Furthermore, the multilayer optical films and processes of post-forming multilayer optical films according to the present invention rely on strain-induced index of refraction differentials between layers in the films. Typically, those differentials will not be expressed herein numerically. Where they are discussed with reference to specific indices of refraction, however, it should be understood that the values used are determined using light having a wavelength of 632.8 nanometers.

As used herein, the terms "reflection" and "reflectance" and variations thereof refer to the reflectance of light rays from a surface. Similarly, the terms "transmission" and "transmittance" and variations thereof are used herein in reference to the transmission of light through a surface, optical stack, film, etc. Except where dyes or colorants are intentionally added, the optical stacks of the present invention preferably exhibit low or minimal absorption losses (typically less than 1% of incident light), and substantially all of the incident light that is not reflected from the surface of an optical stack will be transmitted therethrough.

Multilayer Optical Films

Many multilayer optical films used in connection with the present invention and methods of manufacturing them are described in U.S. patent application Ser. No. 08/402,041 (filed on Mar. 10, 1995); U.S. patent application Ser. No. 08/479,319 (filed Jun. 7, 1995); and U.S. Patent Application Ser. Nos. 09/006,085; 09/006,118; 09/006,288; 09/006,455; 09/006,591 (all filed on Jan. 13, 1998); as well as in various other patents and patent applications referred to herein. Briefly, however, multilayer optical films as used herein refers to optical films including at least one birefringent material provided in contiguous layers with at least one other material such that desired strain-induced refractive index differentials are provided between the layers making up the films. The multilayer optical films preferably exhibit relatively low absorption of incident light, as well as high reflectivity for both off-axis and normal light rays.

The reflective properties generally hold whether the films are used for pure reflection or reflective polarization of light. The unique properties and advantages of multilayer optical films provides an opportunity to design highly reflective post-formed articles that exhibit low absorption losses. One multilayer optical film used in the methods and articles of the present invention is illustrated in FIG. 1 and includes a multilayer stack 10 having alternating layers of at least two materials 12 and 14.

The multilayer optical films according to the present invention all include an optically active portion that will be referred to herein as the "optical stack," i.e., those layers that provide the desired reflective properties of the multilayer optical films by virtue of the refractive index differentials within the optical stack. Other layers and/or materials may be provided in addition to the optical stack. For example, skin layers may be provided on the outside of the optical stack to improve the mechanical properties of the films or provide some other desired property or properties including secondary optical effects such as retardation or polarization conversion, but the bulk of the reflective optical characteristics of the films are determined by the properties of the optical stacks.

Although only two layers 12 and 14 are illustrated, it will be understood that the optical stack of the multilayer optical film 10 can include tens, hundreds or thousands of layers, and each layer can be made from any of a number of different materials, provided that at least one of the materials is birefringent. The characteristics which determine the choice of materials for a particular optical stack depend upon the desired optical performance of the film. The optical stack may contain as many materials as there are layers in the stack. For ease of manufacture, however, preferred optical thin film stacks contain only a few different materials. Some considerations relating to the selection of materials for the optical stacks of multilayer optical films of the present invention are discussed below in the section entitled "Materials Selection."

The boundaries between the materials, or chemically identical materials with different physical properties, within the stack can be abrupt or gradual. Except for some simple cases with analytical solutions, analysis of the latter type of stratified media with continuously varying index is usually treated as a much larger number of thinner uniform layers having abrupt boundaries but with only a small change in properties between adjacent layers.

Further considerations relating to the selection of materials and manufacturing of such multilayer optical films can be obtained with reference to U.S. patent application Ser. No. 08/402,041 (filed on Mar. 10, 1995) and U.S. patent application Ser. Nos. 09/006,085; 09/006,118; 09/006,288; 09/006,455; 09/006,591 (all filed on Jan. 13, 1998).

The preferred optical stack is comprised of low/high index pairs of film layers, wherein each low/high index pair of layers has a combined optical thickness of ½ the center wavelength of the band it is designed to reflect at normal incidence. The optical thickness is the physical layer thickness multiplied by the index of refraction of the material in the layer for a given wavelength and polarization plane cross-section. Stacks of such films are commonly referred to as quarterwave stacks.

As indicated above, at least one of the materials is birefringent, such that the index of refraction (n) of the material along one direction is affected by stretching the material along that direction. The indices of refraction for each layer are n1x, n1y, and n1z for layer 12, and n2x, n2y, and n2z for layer 14. For the purposes of the present invention, the x and y axes will generally be considered to lie within the plane of the film and be perpendicular to each other. The z axis will be perpendicular to both the x and y axes and will generally be normal to the plane of the film.

The stack 10 can be stretched in two (typically) perpendicular in-plane directions to biaxially orient the birefringent material in the layer 14, or the stack 10 may be stretched in only one in-plane direction (uniaxially oriented). By stretching the multilayer stack over a range of uniaxial to biaxial orientation, a film can be created with a range of reflectivities for differently oriented incident light. The multilayer stack can thus be made useful as reflective polarizers or mirrors.

If the stack 10 is stretched in the x and y directions, each adjacent pair of layers 12 and 14 exhibit refractive index differentials between layers in each of the two mutually perpendicular in-plane directions (x & y). The values of the refractive index differentials can be represented by $\Delta x$ (which is equal to (n1x−n2x) where n1x is greater than n2x) and $\Delta y$ (where $\Delta y$=n1y−n2y). It will be understood that a reflective polarizer will preferably exhibit a $\Delta x$ in stack 10 that is sufficiently high to achieve the desired reflectivity and, further, that the stack 10 will exhibit a $\Delta y$ that is sufficiently low such that a substantial percentage of light with coincident polarization is transmitted.

An important parameter for improving the reflectivity of multilayer optical films at oblique angles of incidence is the control of n1z and n2z in relation to the other indices. First assume that n1x is the larger of n1x and n2x such that $\Delta x$ is positive and $|\Delta x|>|\Delta y|$. To increase the reflectivity of the multilayer optical stack at oblique angles of incidence compared to normal incidence, it may be preferred that $\Delta z<\Delta x$. More preferably, $\Delta z=0$, and even more preferably $\Delta z<0$.

For reflective mirror films, the desired average transmission for light of each polarization and plane of incidence generally depends upon the intended use of the reflective film. The average transmission at normal incidence for any polarization direction for a narrow bandwidth reflective film, e.g., a 100 nanometer bandwidth within the visible spectrum is desirably less than 30%, preferably less than 20% and more preferably less than 10%. A desirable average transmission along each polarization direction at normal incidence for a partial reflective film ranges anywhere from, for example, 10% to 50%, and can cover a bandwidth of anywhere between, for example, 100 nanometers and 450 nanometers, depending upon the particular application.

For a high efficiency reflective mirror film, average transmission at normal incidence for any polarization direction over the visible spectrum (400–700 nm) is desirably less than 10%, preferably less than 5%, more preferably less than 2%, and even more preferably less than 1%. The average transmission at 60 degrees from the normal axis for any plane of incidence and polarization direction for a high efficiency reflective film from 400–700 nanometers is desirably less than 10%, preferably less than 5%, more preferably less than 2%, and even more preferably less than 1%.

In addition, asymmetric reflective films may be desirable for certain applications. In that case, average transmission for one polarization direction may be desirably less than, for example, 50%, while the average transmission along another polarization direction may be desirably less than, for example 20%, over a bandwidth of, for example, the visible spectrum (400–700 nanometers), or over the visible spectrum and into the near infrared (e.g., 400–850 nanometers).

In summary, multilayer optical films used in the methods and articles of the present invention include a multilayer stack 10 having alternating layers of at least two diverse polymeric materials 12 and 14, at least one of which preferably exhibits birefringence, such that the index of refraction of the birefringent material is affected by stretching. The adjacent pairs of alternating layers preferably exhibit at least one strain-induced refractive index differential ($\Delta x$, $\Delta y$) along at least one of two perpendicular in-plane axes as discussed briefly below. The selection of materials and/or the orientation process conditions can be used to control the value of $\Delta z$ in relation to the values of $\Delta x$ and $\Delta y$.

By stretching the multilayer stack over a range of uniaxial to biaxial orientation, a multilayer optical film can be created with a range of reflectivities for differently oriented plane polarized light along with the plane of incidence or polarization parallel to various film axes (typically corresponding to the stretch directions) based on the values of $\Delta x$, $\Delta y$, and $\Delta z$. Preferably, those refractive index differentials are generally uniform throughout the film to provide uniform optical properties throughout the film. Variations in those refractive index differentials that fall below desired minimum values for the desired optical characteristics may cause undesirable variations in the optical properties of the films.

Although the articles including post-formed multilayer optical film, the methods of producing those articles, and the post-formable multilayer optical films are often described or explained below with reference to multilayer optical films designed to exhibit broadband reflectance over the visible spectrum, it will be understood that the same concepts could apply to articles, methods and films that exhibit reflectance of light having any desired range or ranges of wavelengths and any desired polarizing qualities. In other words, the present invention is useful with both polarizing multilayer optical films (that preferentially reflect light of one polarization orientation while transmitting light with the orthogonal polarization orientation), as well as multilayer optical films that provide uniform properties for light having any polarization orientation.

Post-Forming of Multilayer Optical Films

As used in connection with the present invention, post-forming can include a variety of processes designed to produce articles having a variety of shapes different from the smooth, planar-surfaced film shape of the multilayer optical film as manufactured. Preferred manufacturing processes involve casting or otherwise forming the film, followed by stretching the film in one direction for a uniaxially stretched film. If the film is to be biaxially stretched, it is typically stretched in both the longitudinal (i.e., machine) direction and in the cross-web direction although any two directions may be used (preferably two generally perpendicular directions). Both uniaxially and biaxially stretched multilayer optical films are manufactured as generally smooth, planar films with caliper or thickness variations of about ±5% or less as manufactured.

Post-forming, as discussed with respect to the present invention, involves further processing of the optical stacks in the multilayer optical films to obtain some permanent deformation in the optical stack. The deformation will preferably involve thinning of the optical stack and it may also involve deforming at least one surface of the film from the uniformly smooth, planar-surfaced film shape in which it is manufactured.

Because the deformations may cause the planarity of the optical stack to be disrupted, it should be understood that, where discussed, the in-plane directions are considered to be relative to a localized area of the optical stack or a point on the optical stack. For a curved optical stack, the in-plane axes can be considered to lie in a plane defined by the tangent lines formed at a particular point on the optical stack. The z-axis would then be perpendicular to that plane.

Post-forming may also include embossing in which the optical layers of the multilayer optical film, i.e., those layers responsible for the reflective properties of the multilayer optical film, are deformed to produce a change in the optical properties of the film. Embossing that provides a textured surface to a skin layer without significantly affecting the optical properties of the optical layers within the multilayer optical film is not considered post-forming within the meaning of that term as used herein. Embossing of a multilayer colored mirror films has been discussed in, e.g., U.S. patent application Ser. Nos. 08/999,624 and 09/006,086.

As can be seen in the embodiments discussed below, post-formed articles are produced by deforming a generally smooth, planar-surfaced film or sheet material to an article having three-dimensional characteristics. Articles including post-formed multilayer optical film can include post-formed multilayer optical film having relatively small deformations such as those experienced as a result of embossing the optical layers of the multilayer optical film, up to larger scale deformations such as thermoformed multilayer optical film used in, e.g., a deep lamp cavity, having a high aspect ratio (i.e., depth to width ratio).

Post-forming operations will typically, but not necessarily, employ heat to improve the working qualities of the multilayer optical film. The post-forming processes may also employ pressure, vacuum, molds, etc. to further improve the working qualities of the multilayer optical film, as well as increase the throughput of the process. For example, one typical post-forming method is thermoforming, including the various forms of vacuum or pressure molding/forming, plug molding, etc. Post-forming may also include re-drawing or stretching films or portions/areas of films in planar directions or stretching the films into non-planar or curved shapes.

It may be helpful to further describe post-forming in terms of the amount of draw induced in the optical stack. In general, post-forming can involve a texturing of the optical stack, shallow drawing of the optical stack, and deep drawing of the optical stack. In the cases where the post-forming involves texturing and/or shallow drawing, it may be possible to use both fully drawn and underdrawn multilayer optical films (as described below) to perform the methods because the draw ratios to be experienced may be relatively small. When performing deep draws, however, it may be advantageous to use underdrawn optical stacks because of their increased extensibility as compared to fully-drawn multilayer optical films. Some exemplary post-forming processes and the articles manufactured thereby are presented below.

One approach to characterizing deformation of the optical stack in a post-formed multilayer optical film according to the present invention is depicted in FIGS. 2 and 2A–2C. The optical stack 20 includes a first major side 24 and a second major side 26 (see FIG. 2A). Also illustrated are selected areas 22 in which the optical stack 20 has been deformed. The selected areas 22 are depicted as being substantially uniform in size and arranged in regular, repeating pattern. It will however, be understood that the selected areas 22 may be non-uniform and/or provided in pattern that irregular/non-repeating.

Figure 2:
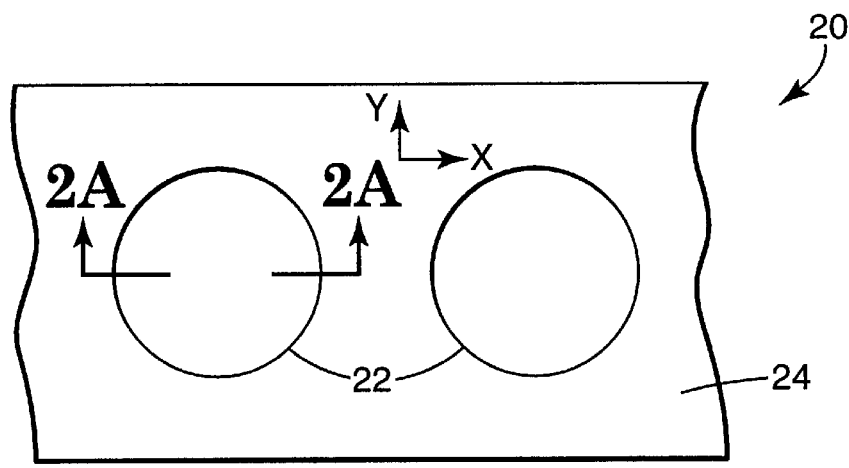
FIG. 2 is a plan view of a portion of one post-formed multilayer optical film according to the present invention including areas deformed along two in-plane directions.
Figure 2A:
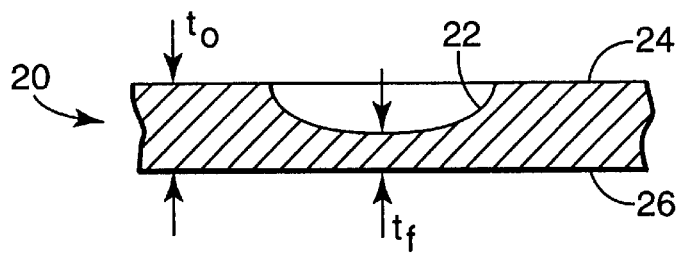
FIG. 2A is an enlarged partial cross-sectional view of the post-formed ultilayer optical film of FIG. 2 taken along line 2A—2A.

One of the selected areas 22 and the surrounding optical stack 20 is seen in the enlarged, partial cross-sectional view of FIG. 2A. The result of the post-forming is that the thickness of the optical stack 20 varies. One of the ways in which that variation can manifest itself is that each of the selected areas 22 can form a depression in the otherwise generally smooth, planar first major side 24 of the optical stack 20. This post-forming may be considered as one example of texturing, i.e., causing deformations in one surface 24 of the optical stack 20 that do not necessarily find any corresponding deformation on the opposite surface 26 of the optical stack 20. Texturing does, however, differ from embossing of skin layers in that the optical stack 20 is itself deformed.

Figure 2B:
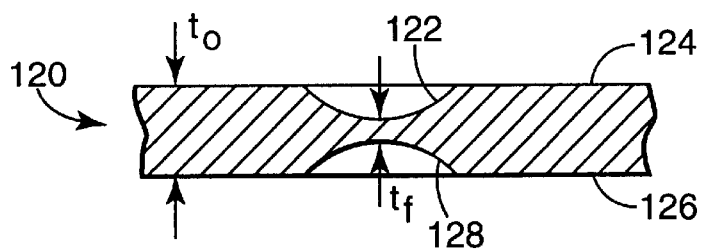
FIGS. 2B and 2C are enlarged partial cross-sectional views of alternative post-formed multilayer optical films deformed along two in-plane directions.

Another manifestation of the thickness variations in an optical stack 120 is illustrated in FIG. 2B where both the first and second major sides 124 and 126 are deformed in selected areas 122 and 128. Like selected area 122 on the first major side 124, selected area 128 on the second major side 126 is also formed as a depression in the otherwise generally smooth planar second major side 126. This is one example of a shallow draw that could be caused by pressure or by strain.

Figure 2C:
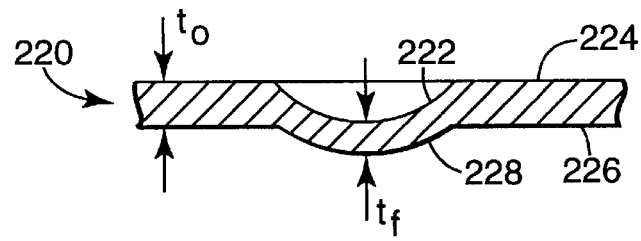

Yet another manifestation of the thickness variations in an optical stack 220 is illustrated in FIG. 2C where both the first and second major sides 224 and 226 are deformed in selected areas 222 and 228. While selected areas 222 are formed as depressions on the first major side 224, the selected area 227 on the second major side 226 is formed as a raised area extending outwards from the otherwise generally smooth, planar second major side 226. As depicted, it may be preferred that the raised area 228 on the second major side 226 be located opposite the depressed area 222 on the first major side 224.

The post-forming result depicted in FIG. 2C is another example of what could be considered a shallow draw, i.e., deformation of the optical stack 220 in the opposing sides 224 and 226 of the optical body 220.

Figure 3:
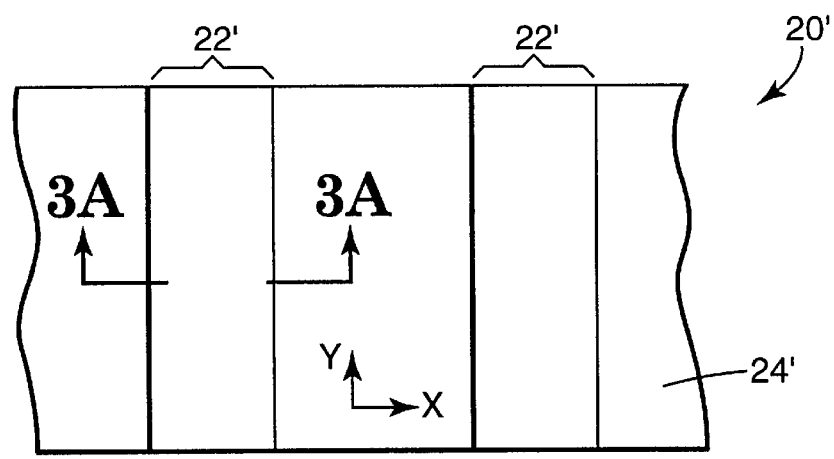
FIG. 3 is a plan view of a portion of one post-formed multilayer optical film according to the present invention including areas deformed along one in-plane direction.

FIG. 3 and cross-sectional views 3A–3C illustrate an alternative embodiment of a post-formed multilayer optical film according to the present invention. The optical stack 20' includes a first major side 24' and a second major side 26' (see FIG. 3A). Also illustrated are selected areas 22' in which the optical stack 20' has been deformed. The selected areas 22' are depicted as being substantially uniform in size. It will however, be understood that the selected areas 22' may be non-uniform.

Referring back to FIG. 2, the selected areas 22 of optical stack 20 are deformed along both in-plane axes (x & y). In contrast, the selected areas 22' of optical stack 20' are preferably deformed along only one in-plane axis (the x axis in FIG. 3). If the optical stack 20' is designed to operate as a reflective polarizer in he deformed areas 22', it may be desirable to deform those areas in the direction of maximum index difference. That should reduce post-forming extension in the matched refractive index direction. As a result, the reflective performance of the polarizing optical stack 20' may be better maintained and, in some cases, increased extension along the proper direction may increase the desired reflectivity of the optical stack 20'.

Figure 3A:
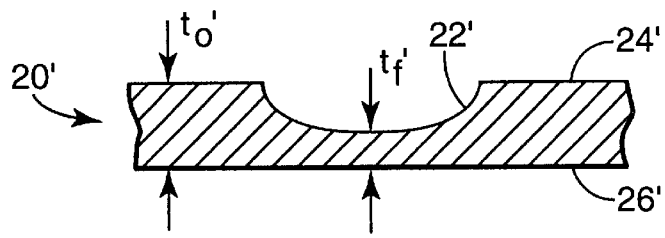
FIG. 3A is an enlarged partial cross-sectional view of the post-formed multilayer optical film of FIG. 3 taken along line 3A—3A.

One of the selected areas 22' and the surrounding optical stack 20' is seen in the enlarged, partial cross-sectional view of FIG. 3A. The result of the post-forming is that the thickness of the optical stack 20' varies. One of the ways in which that variation can manifest itself is that each of the selected areas 22' can form a depression in the otherwise generally smooth, planar first major side 24' of the optical stack 20'.

Figure 3B:
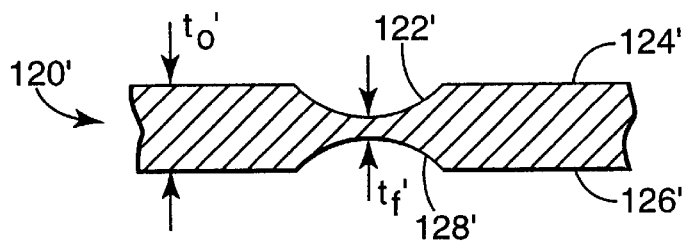
FIGS. 3B and 3C are enlarged partial cross-sectional views of alternative post-formed multilayer optical films deformed along one in-plane direction.

Another manifestation of the thickness variations in an optical stack 120' is illustrated in FIG. 3B where both the first and second major sides 124' and 126' are deformed in selected areas 122' and 128'. Like selected area 122' on the first major side 124', selected area 128' on the second major side 126' is also formed as a depression in the otherwise generally smooth, planar second major side 126'.

Figure 3C:
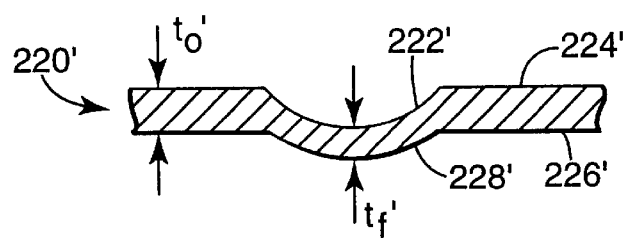

Yet another manifestation of the thickness variations in an optical stack 220' is illustrated in FIG. 3C where both the first and second major sides 224' and 226' are deformed in selected areas 222' and 228'. While selected areas 222' are formed as depressions on the first major side 224', the selected area 227' on the second major side 226' is formed as a raised area extending outwards from the otherwise generally smooth, planar second major side 226'. As depicted, it may be preferred that the raised area 227' on the second major side 226' be located opposite the depressed area 222' on the first major side 224'.

The deformations illustrated in FIGS. 2A–2C and 3A–3C can be characterized by the ratio of the thickness to in the undeformed portions of the optical stacks to the thickness tf of the deformed portions of the optical stacks. Both of those thicknesses are preferably measured between the major surfaces of the optical stacks, i.e., the thickness of any skin layers is not considered. Typically, it may be desirable that the ratio $t_o:t_f$ be at least about 1.1:1 or greater. In some cases, it is desirable that the ratio $t_o:t_f$ be at least about 1.5:1 or greater, more preferably at least about 1.75:1 or greater, and even more preferably at least about 2:1 or greater.

Figure 4:
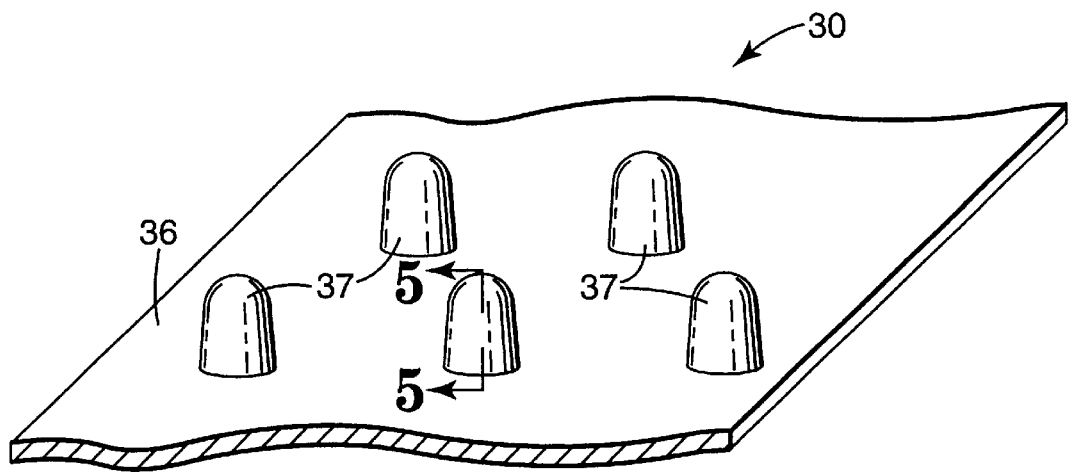
FIG. 4 is a perspective view of a portion of one post-formed multilayer optical film according to the present invention.
Figure 5:
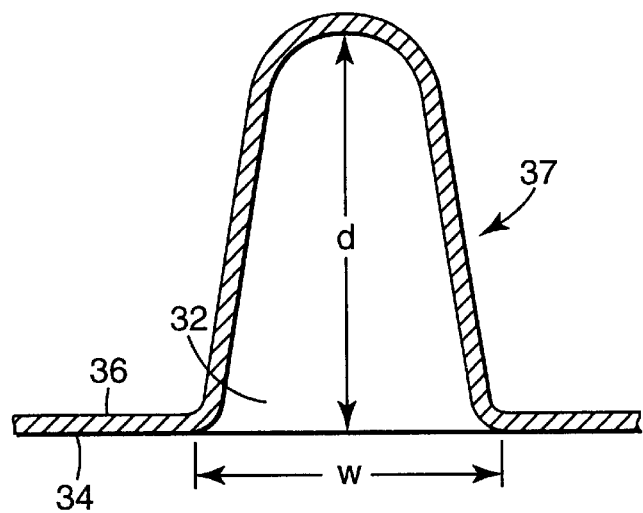
FIG. 5 is an enlarged partial cross-sectional view of the multilayer optical film of FIG. 4 taken along line 5—5 in FIG. 4.

FIGS. 4 & 5 illustrate a more extreme example of the post-formed optical stack 220 illustrated in FIG. 2C. The post-formed optical stack 30 illustrated in FIGS. 4 & 5 can be considered an example of a deep draw post-forming process. The optical stack 30 of FIG. 4 includes a first major side 34 (see FIG. 5) and a second major side 36 along with a plurality of selected areas 32 in which the optical stack 30 has been post-formed to provide depressed areas 32 formed on the first major side 34 of the optical stack and raised areas 37 formed on the second major side 36 of the optical stack 30.

The deformed areas of the deeply drawn optical stack can be characterized by the aspect ratio of the width (w) of the depressed areas 32 as measured across the opening 33 of the depressed area 32 to the depth (d) of the depressed areas 32 as measured from the first major side 34 of the optical stack 30. It is preferred that the width of the depressed area 32 be measured across its narrowest dimension. It may be desirable that the depressed areas 32 have an aspect ratio w:d of about 10:1 or less, more desirably 2:1 or less, even more desirably about 1:1 or less, and still more desirably about 0.5:1 or less.

Alternatively, the deformation in the optical stack 30 can be measured in absolute terms. For example, it may be preferred that the depth d be at least about 0.1 millimeter or more; more preferably at least about 1 millimeter or more; and even more preferably at least about 10 millimeters or more. It will be understood that where the depth d of the depressed areas 32 approaches or exceeds the thickness of the optical stack 30, the more likely it is that a raised area 37 will be formed on the second major side 36 of the optical stack.

Figure 6:
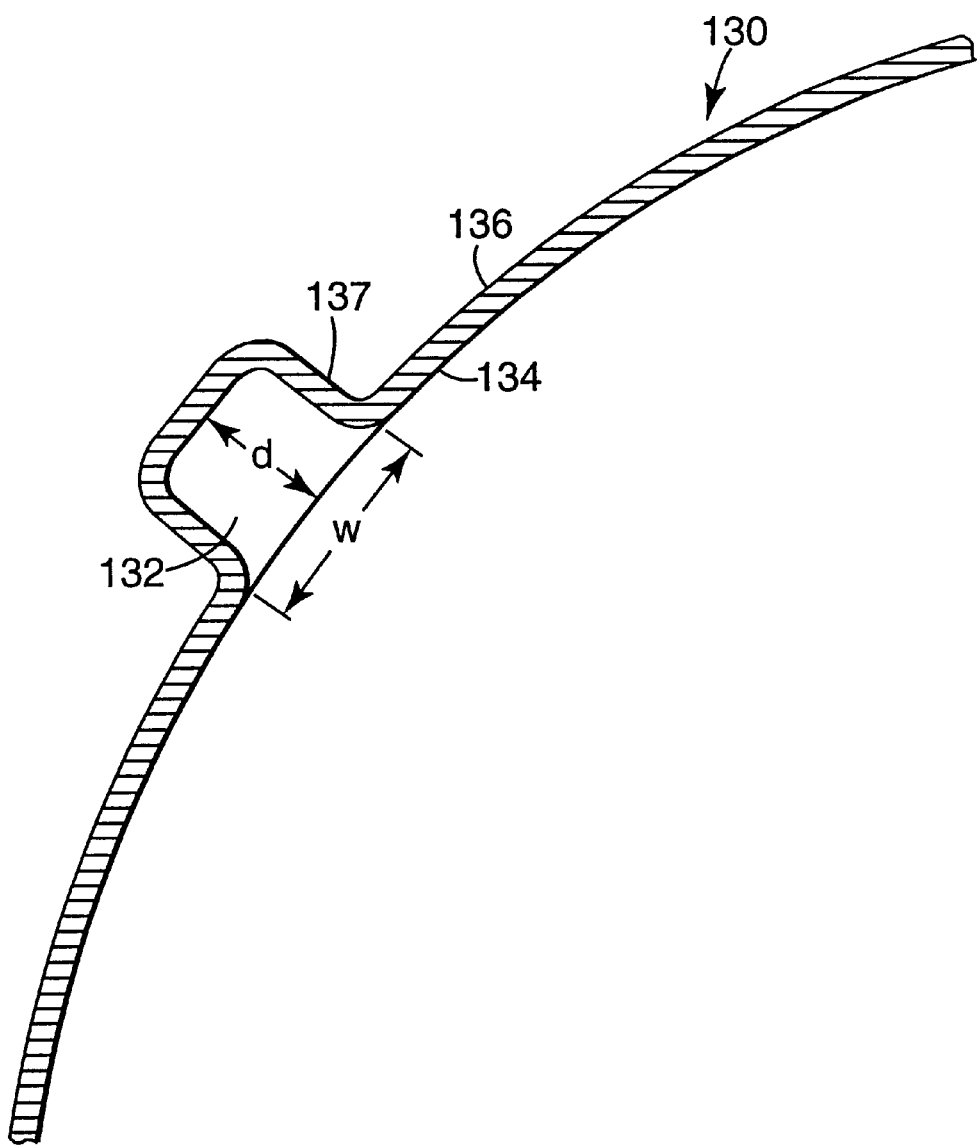
FIG. 6 is a partial cross-sectional view of another post-formed multilayer optical film according to the present invention.

The measurement of the depth d of the depressed areas 32 formed on the first major side 34 of the optical stack 30 is not limited to those instances in which the first major side is planar. Turning now to FIG. 6, where the optical stack 130 of a multilayer optical film is depicted in a curved configuration. The optical stack 130 includes a depressed area 132 formed on the first major side 134 of the optical stack 130 and a corresponding raised area 137 on the second major side 136 of the optical stack 130. The depth d of the depressed area 132 will preferably be measured from the geometric surface defined by the first major side 134 of the optical stack 130 and will typically be the largest depth from that geometric surface.

Figure 7:
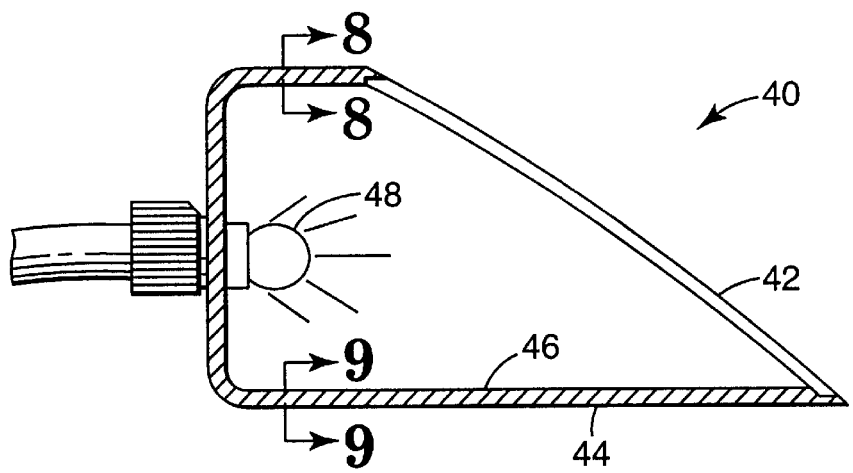
FIG. 7 is a partial cross-sectional view of a dental operatory light assembly including post-formed multilayer optical film according to the present invention.
Figure 8:
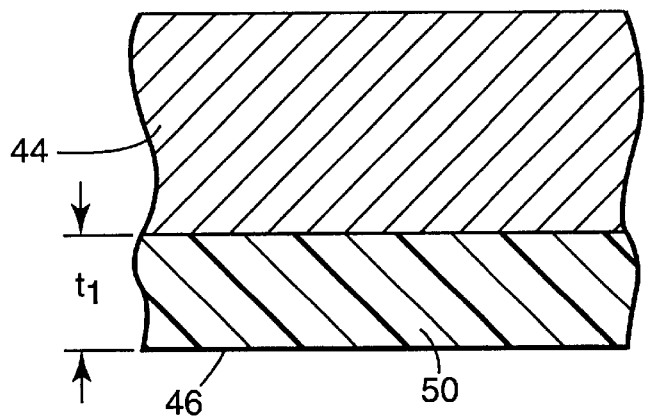
FIG. 8 is an enlarged cross-sectional view of one portion of the dental operatory light assembly of FIG. 7 taken along line 8—8.
Figure 9:
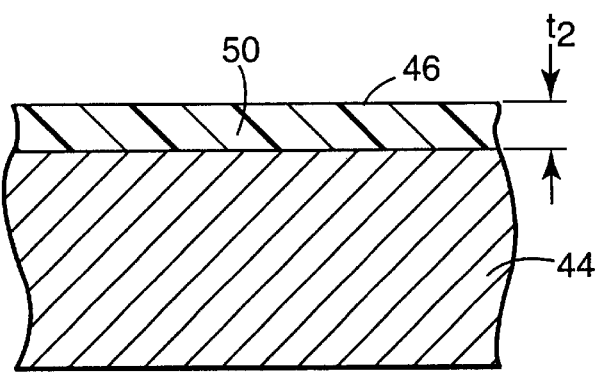
FIG. 9 is an enlarged cross-sectional view of one portion of the dental operatory light assembly of FIG. 7 taken along line 9—9.

FIGS. 7–9 depict one illustrative dental article including post-formed multilayer optical film. FIG. 7 is a cross-sectional view of a dental operatory light assembly 40. The light assembly 40 includes a lens 42, a lamp cavity 44 having a reflective inner surface 46, and a light source 48 mounted within the lamp cavity 44.

When used in connection with photo-curing dental materials, it may be preferred to limit the transmission of light through the lens 42 such that the photo-curing wavelength or wavelengths of light are not transmitted through the lens 42. By limiting the transmission of those selected wavelengths of light, the working time of the photo-curing materials may be extended. As depicted, the lenses of dental operatory lights such as lens 42 may be non-planar.

Typically, the photochemical reaction in many dental materials is initiated by high intensity blue light having wavelengths in the range of from about 420 nanometers to about 500 nanometers. As a result, one preferred range of wavelengths either transmitted or reflected from the post-formed multilayer optical films used in dental articles according to the present invention extends from about 420 nanometers to about 500 nanometers. The choice of selective reflection or transmission is based on the intended effect and the actual article as will be discussed below.

FIG. 8 is an enlarged cross-sectional view of the lamp cavity 44 taken along line 8—8 in FIG. 7, and FIG. 9 is an enlarged cross-sectional view of the lamp cavity 40 taken along line 9—9 in FIG. 7. Both of the views depict a layer of post-formed multilayer optical film 50 on the inner surface 46 of the lamp cavity 44. Because the multilayer optical film 50 typically lacks sufficient structural rigidity alone, it may be preferred to mount the multilayer optical film 50 on a substrate 52 or some other form of structural support, e.g. a frame, etc., by any suitable technique.

It may also be preferred that the reflective inner surface 46 of the lamp cavity 44 include post-formed multilayer optical film manufactured according to the principles of the present invention. In dental operatory lights in which the lens 42 does not transmit (i.e., reflects) light in the photo-curing wavelength or wavelengths, it may be preferred that the multilayer optical film used for the inner surface 46 be highly reflective for visible light and it may also be helpful if the multilayer optical film is also reflective for light into the infrared spectrum to limit heat build-up of the lamp cavity 44 due to absorption of infrared energy by the substrate on which the reflective inner surface 46 is located. Alternatively, if the multilayer optical film has sufficient structural integrity such that entire lamp cavity 44 is constructed of the multilayer optical film, it may be preferable that the multilayer optical film be transmissive for infrared energy to limit heat build-up within the light assembly 40.

In another variation, the multilayer optical film used for the inner surface 46 of the light assembly 40 may be transmissive for light in the photo-curing wavelength or wavelengths to reduce or prevent its delivery out of the lens 42. If the multilayer optical film used on the inner surface 46 of the lamp cavity 44 is attached to a substrate material, that material may absorb or transmit the photo-curing light such that it is not available for reflection through the lens 42 and into the patient's mouth.

One advantage of using multilayer optical film for the reflective inner surface 46 of the lamp cavity 44 is the high reflectivity of the multilayer optical film. Even if the multilayer optical film is tuned to not reflect (i.e., transmit) light in the photo-curing wavelength or wavelengths, the remaining light in the visible spectrum will typically be reflected with high efficiency, thereby improving illumination of the patient's mouth.

As seen in FIGS. 7–9, the lamp cavity 44 and lens 42 of the light assembly 40 include a number of non-planar shapes that require some post-forming of the multilayer optical film used in the light assembly 40. Post-forming processes do not typically deform a multilayer optical film uniformly and, as a result, the thickness of the optical stacks in post-formed multilayer optical films according to the present invention vary. The variations in thickness of the post-formed multilayer optical film are in direct contrast with the controlled uniform thickness of the multilayer optical film as manufactured. That uniform thickness is desired because the thickness of the optical layers within the multilayer optical film define, in part, its optical properties. As a result, variations in the multilayer optical film as manufactured are not desired because they can adversely impact the uniform optical properties of the film. For example, non-uniformities in the optical stack of multilayer optical film as manufactured can result in iridescence or other optical artifacts and may, in some instances result in the undesired reflection or transmission of light in the photo-curing wavelength or wavelengths.

Thickness variations in the optical stack of post-formed multilayer optical film are, in large part, caused by variations in the strain experienced in different areas of the multilayer optical film during post-forming. In other words, some areas of the post-formed multilayer optical film may experience significant deformation (strain) while other areas may experience little or no deformation during post-forming.

The optical stacks of post-formed multilayer optical film in articles will, as a result, often include variations in thickness as illustrated in FIGS. 3A–3C, 8 and 9. For example, the thickness of the multilayer optical film 50 varies between the two points in the lamp cavity 44. The thickness t, of the optical stack of the post-formed multilayer optical film seen in FIG. 8 is thicker than the thickness 12 of the optical stack of the post-formed multilayer optical film depicted in FIG. 9. In both areas, however, it is preferred that the reflectivity of the multilayer optical film 50 for the desired range of wavelengths remains high for normal, as well as off-axis, light. The importance of off-axis reflectivity can be seen in FIG. 7 where light from the light source 48 may approach portions of the light cavity 44 at high angles off of normal.

The thickness variations in the optical stack can cause what is commonly referred to as band shifting. In other words, the range of wavelengths of which any multilayer optical film is reflective is, in part, a function of the physical thickness of the layers in the multilayer optical film. Varying the physical thickness of the layers can cause the range of wavelengths over which the film is reflective to change. Because changes in thickness typically involve thinning of the multilayer optical film from its manufactured thickness, band shifting is usually downward. For example, a multilayer optical film that exhibits broadband reflectance of light with wavelengths over the range of 400–900 nanometers and is thinned by a factor of 2 during post-forming will, after thinning, typically exhibit broadband reflectance for light with wavelengths in the range of 200–450 nanometers.

One approach to compensate for the effects of thinning multilayer optical films (or any multilayer article exhibiting reflectivity as a result of refractive index differentials), is discussed in U.S. Pat. No. 5,448,404 (Schrenk et al.). Essentially, the thinning effect and corresponding band shift can be compensated for by adjusting the bandwidth of the multilayer optical film as manufactured such that, after post-forming, the multilayer optical film has layers with the appropriate optical thickness to reflect light with the desired wavelengths.

Although both the upper and lower band edges may be adjusted to compensate for thinning, for broadband mirrors it may be preferable to adjust only the upper edge of the range of reflected wavelengths upward by a factor that is at least as large as the expected maximum factor by which the multilayer optical film will be thinned during post-forming. By increasing the upper limit of the range of wavelengths over which the multilayer optical film reflects light before post-forming or drawing, the portions of the post-formed multilayer optical film that are thinned during post-forming will maintain their reflectivity over the desired range of wavelengths (assuming the maximum factor by which the multilayer optical film is thinned during post-forming does not exceed the factor by which the upper limit of the wavelength range has been adjusted to account for thinning during post-forming).

For broad band mirrors, it is typically not preferred to adjust the lower limit in the reflected wavelength range because some areas of the multilayer optical film may experience little or no deformation or thinning during post-forming. By supplying a multilayer optical film that, before post-forming, already reflects light at the lower end of the desired range of wavelengths, reflectivity of the entire post-formed multilayer optical film at the lower end of the desired range of wavelengths can be retained after post-forming.

For example, if the post-formed multilayer optical film in the article is to reflect substantially all visible light (i.e., 400–700 nanometer light), then before post-forming the multilayer optical film should reflect normal incident light in at least the wavelength range of from about 400 nanometers to about 900 nanometers multiplied by the expected thinning factor (the increase in the upper edge bandwidth from 700 to 900 nanometers is provided to compensate for light approaching at angles off of the normal axis). If the maximum factor by which the post-formed multilayer optical film is expected to be thinned during post-forming is 2, then the multilayer optical film will preferably reflect normal incident light in at least the wavelength range of from about 400 nanometers to about 1800 nanometers. If the maximum factor by which the post-formed multilayer optical film is expected to be thinned during post-forming is 3, then the multilayer optical film will preferably reflect normal incident light in at least the wavelength range of from about 400 nanometers to about 2700 nanometers.

If the optical stack of a multilayer optical film is designed to compensate for thinning, variations in the thickness of the post-formed multilayer optical film can be allowed without significantly affecting reflectivity of the optical stack over the desired wavelengths. For example, the ratio $t_1:t_2$ in the post-formed multilayer optical film article 50 illustrated in FIGS. 7–9 may be at least about 2:1 or more without significantly affecting the reflective properties of the multilayer optical film.

In some cases, it may be possible to provide multilayer optical films that can support thickness ratios of 3:1 or more without significant degradation of the optical properties of the post-formed multilayer optical film over desired wavelengths.

Figure 10:
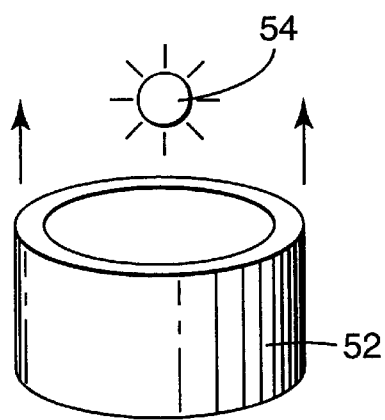

FIG. 10 illustrates another dental article including post-formed multilayer optical film according to the present invention. The article is a light cover 52 that can be placed around or over a light source 54 to reduce or prevent the transmission of selected wavelengths of light into the dental operatory area. As discussed above, it may be desirable to limit the amount of light in the photo-curing wavelength or wavelengths of the photo-curable dental materials being used in a given procedure to prevent premature curing and/or enhance working time with the materials. In many instances, the light covers will be best implemented in a shape that includes curves, corners, etc. that require some post-forming of the normally planar multilayer optical film.

Figure 11:
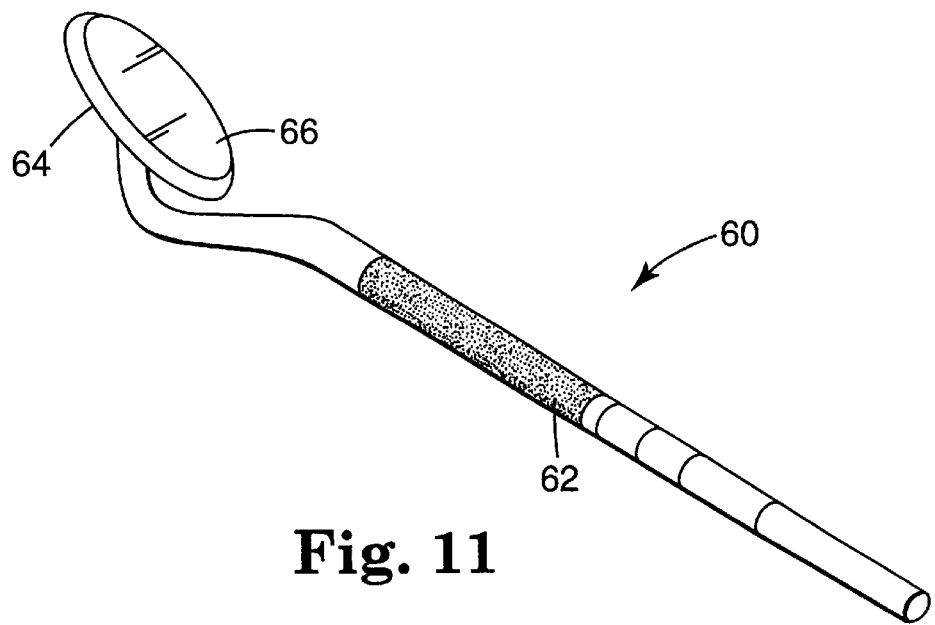
FIG. 11 is a perspective view of a light cover including post-formed multilayer optical film according to the present invention.

Examples of some useful dental implements that include post-formed multilayer optical film are illustrated in FIGS. 11–14. FIG. 11 illustrates a dental mirror 60 including a handle 62 and a head 64. It is preferred that the dental mirror 60 includes an optical surface 66 on the mirror head 64 that is reflective to assist a dental professional in viewing the interior of a patient's mouth.

Advantages of using post-formed multilayer optical film for dental mirrors include the high reflectivity of multilayer optical film. In addition, although conventional dental mirrors are typically manufactured of, e.g., stainless steel, a dental mirror 60 including post-formed multilayer optical film for the mirror surface 66 could be manufactured of, e.g., plastic and post-formed multilayer optical film to provide an inexpensive dental mirror 60 with excellent reflective properties. It may be preferable to dispose of such a mirror after one use rather than subjecting the mirror to sterilization. Alternatively, the mirror 60 could be sterilized between procedures and reused if so desired.

Figure 11A:
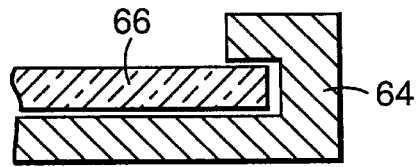
FIG. 11A is an enlarged partial cross-sectional view of the dental mirror of FIG. 11.
Figure 11B:
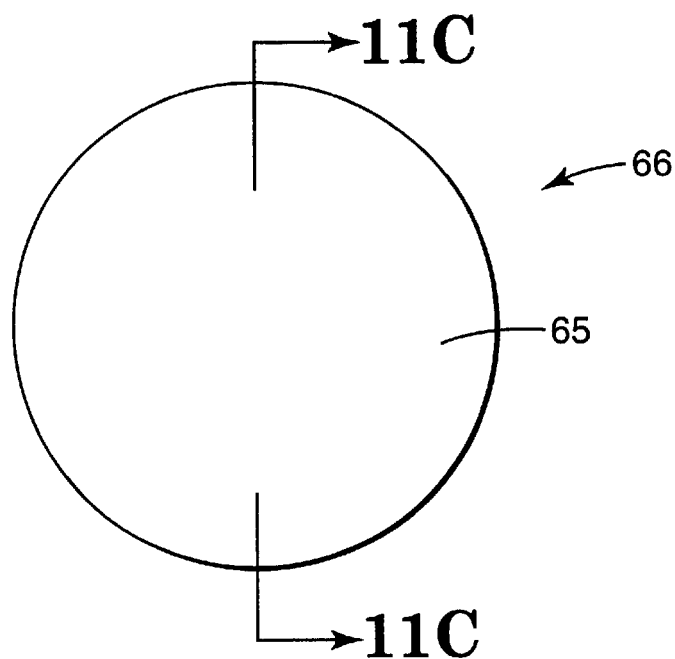
FIG. 11B is a plan view of one dental mirror optical surface.

One alternative construction of the mirror 60 could include a reusable handle 62 and head 64 manufactured of a material that can be repeatedly sterilized without significant adverse effects. The reflective optical surface 66 could then be provided from post-formed multilayer optical film that is attached to the head 64 by, e.g., adhesives, etc. One alternative to adhesive attachment of the post-formed multilayer optical film is illustrated in the enlarged partial cross-sectional view of FIG. 11A in which a slot 68 is provided about the circumference of the mirror head 64 to retain the post-formed multilayer optical film forming the optical surface 66 by mechanical interference. Other techniques, mechanical or otherwise, for retaining a disposable mirror constructed of post-formed multilayer optical film on the head 64 will be known to those skilled in the art.

Another advantage of using post-formed multilayer optical film to provide the optical surface 66 is that the multilayer optical film can be post-formed into a variety of shapes. FIG. 11 B is a plan view of the optical surface 66 of the dental mirror 60. The illustrated optical surface 66 is generally circular, although it will be understood that the optical surface 66 could be formed into any desired shape, e.g., rectangular, oval, elliptical, mouth-shaped, etc.

Figure 11C:
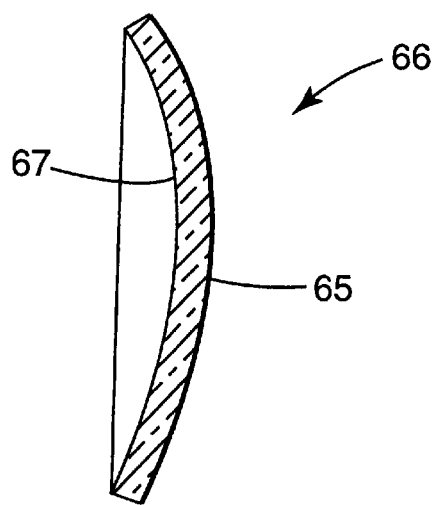
FIG. 11C is a cross-sectional view of the dental mirror optical surface of FIG. 11B taken along line 11C—11C.

In addition to a variety of shapes for the outline of the optical surface 66, the multilayer optical film used for the optical surface 66 can be post-formed into a variety of non-planar shapes to provide a desired optical effect such as increased viewing angle, magnification, etc. As illustrated in the cross-sectional view in FIG. 11C, the side 65 of the optical surface 66 is substantially convex in shape and the opposite side 67 is concave. Either side 65 or 67 could be used as the optical surface of a dental mirror as desired. For example, the concave side 67 could be used as a magnifying mirror while the convex side 65 could be used where a wider viewing angle was desired. A magnifying mirror may be used, for example, by dental professionals or other who do not have a magnifying lens. Convex mirrors may be used to reduce the image to, e.g., assess the alignment of contiguous teeth in, e.g., orthodontics.

Because the multilayer optical film is a film, it may be converted in a variety of manners, such as, e.g., punching, stamping, cutting, laminating, etc. to produce applique-like articles that are easily attached to the mirror head. The formed optical surfaces may be delivered in, e.g., a pop-tape format for dispensing at the point of use or elsewhere.

For those dental implements used in or near the mount, fogging of the optical surface may be a problem. As a result, it may be desirable to provide an anti-fog coating on the optical surface of the dental implement. Various anti-fogging agents are known to the art which are suitable for use with the present invention. Typically, however, these materials will substances, such as fatty acid esters, which impart hydrophobic properties to the surface of the optical body and which promote the formation of a continuous, less opaque film of water.

Coatings which reduce the tendency for surfaces to "fog" have been reported by several inventors. For example, U.S. Pat. No. 3,212,909 to Leigh discloses the use of ammonium soap, such as alkyl ammonium carboxylates in admixture with a surface active agent which is a sulfated or sulfonated fatty material, to produce a anti-fogging composition. U.S. Pat. No. 3,075,228 to Elias discloses the use of salts of sulfated alkyl aryloxypolyalkoxy alcohol, as well as alkylbenzene sulfonates, to produce an anti-fogging article useful in cleaning and imparting anti-fogging properties to various surfaces. U.S. Pat. No. 3,819,522 to Zmoda, discloses the use of surfactant combinations comprising derivatives of decyne diol as well as surfactant mixtures which include ethoxylated alkyl sulfates in an anti-fogging window cleaner surfactant mixture. Japanese Patent Kokai No. Hei 6[1994] 41,335 discloses a clouding and drip preventive composition comprising colloidal alumina, colloidal silica and an anionic surfactant. U.S. Pat. No. 4,478,909 (Taniguchi et al) discloses a cured anti-fogging coating film which comprises polyvinyl alcohol, a finely divided silica, and an organic silicon compound, the carbon/silicon weight ratio apparently being important to the film's reported anti-fogging properties. Various surfactants, include fluorine-containing surfactants, may be used to improve the surface smoothness of the coating. Other anti-fog coatings incorporating surfactants are described in U.S. Pat. Nos. 2,803,552; 3,022,178; and 3,897,356. World Patent No. PCT 96/18,691 (Scholtz et al) discloses means by which coatings may impart both anti-fog and anti-reflective properties.

Figure 12:
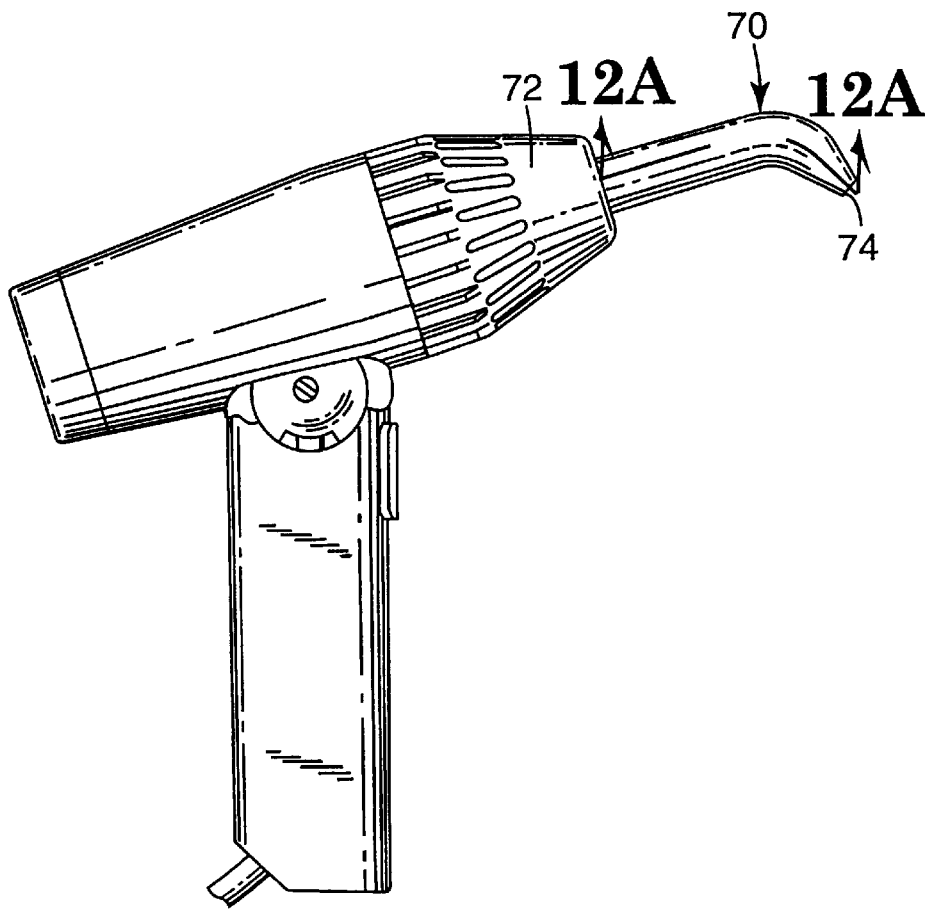
FIG. 12 is a plan view of one dental light guide and light source.

Another example of an article including post-formed multilayer optical film according to the present invention is illustrated in FIGS. 12 and 13. The article 70 is a dental light guide designed specifically for use in the curing of photo-curing dental materials. As seen best in FIG. 12, the light guide 70 is designed for use in a light source 72 which, in the illustrated embodiment, takes the form of a pistol-grip device similar to that described in commonly-assigned U.S. Pat. No. 5,147,204 (Patten et al.). Those skilled in the art will understand that other light sources could be used in connection with light guides manufactured according to the present invention.

At least a portion of the light guide 70 is preferably manufactured as a tube of post-formed multilayer optical film. The ability to post-form the multilayer optical film provides a number of advantages including high reflectivity and light weight. In addition, the light guide 70 may be manufactured as a disposable unit, thereby avoiding the need for sterilization of the light guide 70 between procedures.

Figure 12A:
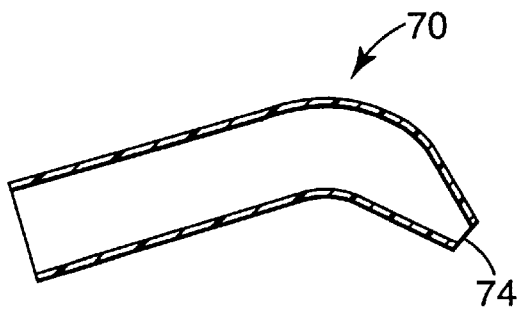
FIG. 12A is a cross-sectional view of the light guide of FIG. 12 taken along line 12A—12A.

Another advantage of a light guide 70 employing post-formed multilayer optical film is that the diameter of the light guide 70 can be varied along its length to construct, e.g., a cone, taper, curved tube, etc. As best seen in the cross-sectional view of the light guide 70 in FIG. 12A, the light guide 70 can taper along its length to provide concentration of light emanating from the light source 72 to the tip 74 of the light guide 70.

Figure 13A:
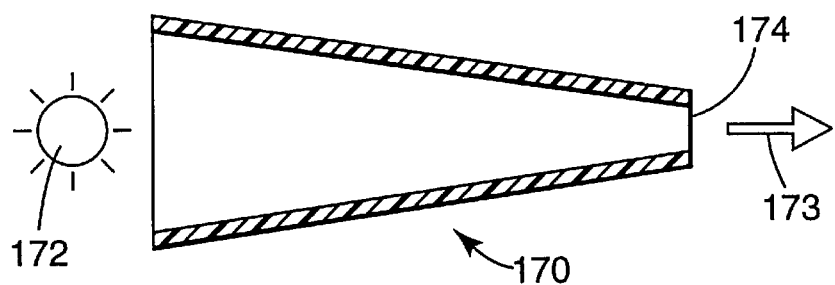
FIGS. 13A—13C are cross-sectional views of alternate dental light guides.
Figure 13B:
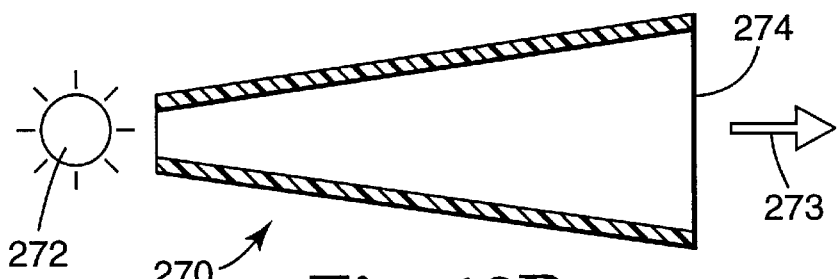
Figure 13C:
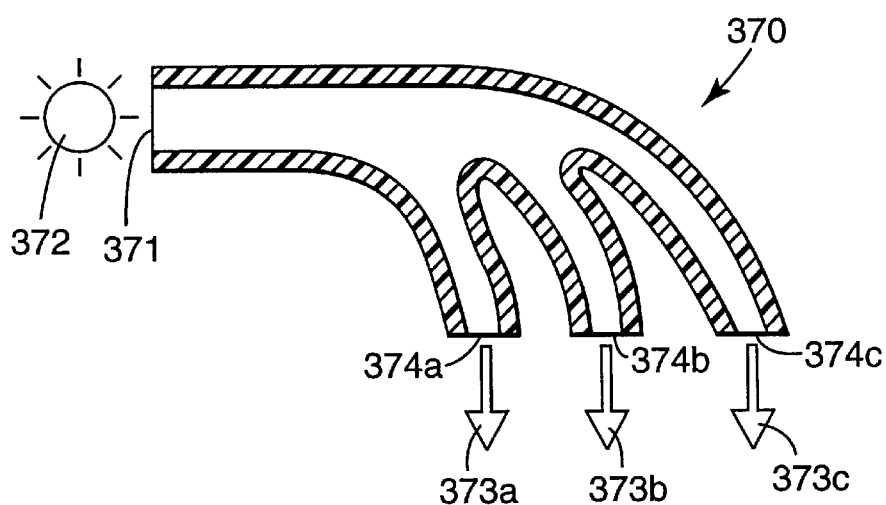

FIGS. 13A–13C depict alternate light guides manufactured from post-formed multilayer optical film according to the present invention. The light guide 170 is depicted in FIG. 13A along with a light source 172. It may be preferred that the light guide 170 operate to at least partially collimate the light 173 exiting the end 164 of the light guide 170 to concentrate the light. Another advantage is that the restricted area of illumination may allow for more precise control of the of the curing light.

The light guide 270 depicted with the light source 272 in FIG. 13B is an example of a light guide that provides for expanded illumination. As seen in FIG. 13B, the light 273 exits the wider end 274 of the light guide 270. The expanded field illuminated by the light 273 can, e.g., assist dental professionals in viewing areas within a patient's mouth.

It should be noted that both light guide 170 and 270 could be manufactured of multilayer optical film that is not post-formed in accordance with the teachings of U.S. patent application Ser. No. 08/494,366 filed on Jun. 26, 1995 titled HIGH EFFICIENCY OPTICAL DEVICES.

The light guide 370 depicted in FIG. 13C is an example of a trifurcated light guide in which light from a single source 372 enters a common opening 371 in the light guide 370. The exiting light 373a, 373b, and 373c exits the light guide 370 at three points 374a, 374b and 374c. Such a light guide could be used to provide light to different locations within a patient's mouth. It should be understood that the light guides of the present invention could alternatively be provide with only two exit points delivering light or four or more exit points depending on the desired number of delivery points.

Among the advantages of light guides constructed of multilayer optical film is the distancing that can be achieved between the light source and the dental material to be cured. In some instances, the light source could be mounted on a stand and the dental professional could be required to handle only the light guide during procedures. Contamination of the patient can be reduced or prevented if the light guides are disposed of after use.

Yet another advantage of light guides manufactured from post-formed multilayer optical film is that the wavelengths over which the multilayer optical film is reflective can be tailored to those wavelengths that are optimal for photo-curing the dental material. As a result, the light guides may be transmissive for light outside of the photo-curing wavelengths. One practical effect of that feature is that the dental professionals may be able to see through the light guide during use.

Although the illustrated light guides are depicted as being manufactured entirely from post-formed multilayer optical film, it will be understood that it may be desirable to provide a support framework in connection with the light guides or that one or more layers of a substrate material as described below may be included to enhance the structural rigidity of the light guides.

Figure 14:
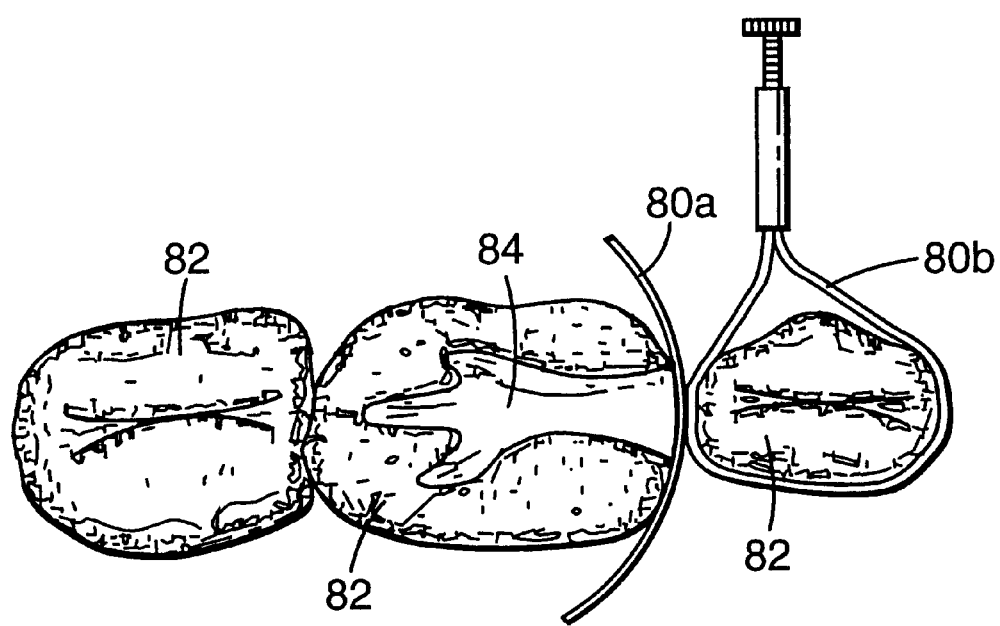
FIG. 14 is a plan view of a dental matrix band manufactured with post-formed multilayer optical film according to the present invention.

FIG. 14 is a plan view of another dental article incorporating post-formed multilayer optical film according to the present invention. The articles 80a and 80b (referred to below as 80) are commonly known as dental matrix bands and are used to mold a particular form or shape for dental restorative materials 81 applied to a void 84 formed in a tooth 82 during a dental operatory procedure. Because many dental restorative materials are photocured, it may be advantageous to provide the dental matrix bands 80 from post-formed multilayer optical film having a desired shape.

It may also be preferred that the multilayer optical film is transmissive in the wavelengths that are relied on for photocuring to assist that process. For example, the multilayer optical film may be transmissive for substantially all of the light in the range of wavelengths of 420–450 nanometers as used in connection with the Visilux 2™ (available from Minnesota Mining and Manufacturing Company, St. Paul, Minn.).

Providing matrix bands that are transmissive may enhance the curing process and increase the depth of cure of the photo-curing dental material. When provided in the shape of a matrix band, the transmissive multilayer optical film enables curing light to reach the dental material through the matrix band as well as from the top of the tooth. As a result, the actual distance the curing radiation must penetrate the dental material may be reduced. That reduction may be particularly advantageous when curing filled and/or highly scattering dental materials.

Alternatively, portions of the multilayer optical film may be transmissive for the photo-curing wavelengths while other portions of the multilayer optical film may be reflective for the photocuring wavelengths. By providing reflective portions of post-formed multilayer optical film, areas may be shielded from the photo-curing wavelengths. Alternatively, the back side 86 of the matrix band, i.e., the portion on the opposite side of the light source 88, may be reflective to the photo-curing wavelengths to enhance curing by reflecting the photo-curing wavelengths of light passing through the dental restorative material 81 back through the material 81 again.

Although some specific examples of dental articles including post-formed multilayer optical film have been described above, it will be understood that post-formed multilayer optical film may be included in the construction of any dental article in which it is desired to take advantage of the unique optical properties of multilayer optical films.

Furthermore, the dental articles according to the present invention may be constructed entirely of post-formed multilayer optical film or they may only include multilayer optical film in their construction. If the post-formed multilayer optical film constitutes only a portion of the article, it will be understood that the post-formed multilayer optical film could be integrated into larger assemblies by any suitable techniques, such as insert injection molding, ultrasonic welding, adhesive bonding, and other techniques.

Underdrawn Multilayer Optical Films

Of the multilayer optical films described in U.S. patent application Ser. No. 08/402,041, the mirror constructions of such films are typically optimized for a high index differential. The films typically have low extensibility limits (i.e., those limits beyond which the films typically deform without fracture or tear during deformation) because they are stretched during manufacturing to levels that provide the desired high index of refraction differential. In addition, some of the multilayer optical films may be heat-set during manufacturing. Heat setting induces further crystallization within the film and that increased crystallization will typically further reduce the extensibility limits of the films.

As a result of their relatively low extensibility limits, known multilayer optical films such as those described in U.S. patent application Ser. No. 08/402,041 may be difficult to post-form without resulting in significant negative effects on the optical properties of the resulting post-formed multilayer optical film. Although the methods described above may be helpful in providing articles including post-formed multilayer optical film and methods of forming the articles, another approach to providing articles including post-formed multilayer optical films can be pursued.

That other approach involves using multilayer optical films in which the extensibility limits of the film are increased for post-forming by deliberate underdrawing of the film during its manufacture to produce what will be described with respect to the present invention as an "underdrawn multilayer optical film" or "underdrawn film". Such underdrawn multilayer optical film can then be provided in a rolls or sheets for use in a subsequent post-forming process or it may be directed into an in-line post-forming process.

Multilayer optical film including layers of one or more birefringent materials alternating with another material may be characterized according to the strain-induced orientation and/or crystallinity of the birefringent materials in the films. In fully drawn films, or at least films considered to be fully drawn for the purposes of the present invention, the birefringent materials will typically exhibit higher levels of orientation and/or crystallinity than a corresponding multilayer optical film constructed of the same materials that is underdrawn.

The higher level of crystallinity in the fully drawn films is, in large part, the result of the increased effective strain to which the multilayer optical film is subjected during manufacturing. As discussed above, fully drawn films are typically drawn to higher levels to improve their reflective properties. Those reflective properties are largely based on the orientation and/or crystallinity of the birefringent materials in the film, which can be correlated to the index of refraction of the birefringent materials. As a result, orientation and/or crystallinity are also related to the refractive index differentials ($\Delta x$, $\Delta y$) in any multilayer optical film.

Because an underdrawn multilayer optical film is not subjected to the same level of effective strain as is a fully drawn multilayer optical film with the same construction, the birefringent material in the underdrawn multilayer optical film will typically exhibit reduced crystallinity or at least one reduced in-plane refractive index differential ($\Delta x$ or $\Delta y$) as compared to a fully drawn multilayer optical film manufactured with the same materials, layer thicknesses, numbers of layers, etc.

The reduced orientation and/or crystallinity may also typically result in reduced refractive index differentials in the underdrawn multilayer optical films as compared to the same construction in a fully drawn state. As a result, it may be helpful to increase the number of layers usually required to cover a given wavelength range with a given reflectance. Second order peaks from the thicker layers of the broader band may reduce the actual need for an increase in the layer numbers. Such considerations can, however, be determined based on the discussions in U.S. patent application Ser. No. 08/402,041.

It is important to note that, in addition to an upper limit on crystallinity for an underdrawn multilayer optical film, there is also preferably a lower limit as well. In other words, an underdrawn multilayer optical film including birefringent materials in its layers will include at least some level of strain-induced crystallinity. By providing underdrawn multilayer optical films with at least some level of strain-induced crystallinity, the post-forming of the underdrawn multilayer optical films will typically be more predictable as compared to a film in which no strain-induced crystallization is found in the birefringent materials.

Figure 15:
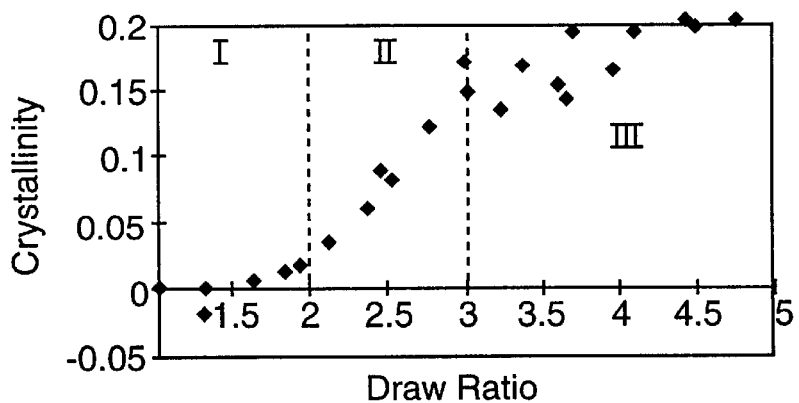
FIG. 15 is a graph illustrating the relationship between draw ratio (horizontal axis) and crystallinity (vertical axis) in the birefringent materials of a multilayer optical film.

The importance of providing an underdrawn multilayer optical film with at least some strain-induced crystallinity is illustrated in FIG. 15, an idealized graph of draw ratio (horizontal axis) versus crystallinity (vertical axis) for multilayer optical films including layers of at least one birefringent material alternating with another material. The behavior illustrated in FIG. 15 is typical of polyesters such as PEN, PET or co-polymers comprising them which can develop birefringence and which can be cast from a die and quenched efficiently resulting in an initial cast web or film with very little crystallinity. FIG. 15 may also characterize other quenchable, birefringent polymeric materials that are susceptible to strain-induced crystallization. Again, such quenched films would preferably exhibit only low levels of crystallinity caused by crystallization during quenching prior to drawing. As drawing of the film is begun, the crystallinity of the birefringent materials in the multilayer optical film may begin to increase, but the increases are at relatively low initial rates. Those draw ratios at which the strain-induced crystallinity increases at a relatively low initial rate are included in what will be defined as Regime I for the purposes of the present invention. As the draw ratio increases past Regime I into what will be referred to as Regime II, the crystallinity of the birefringent material in the multilayer optical film as a function of the draw ratio increases at a significantly faster rate than in Regime I.

In Regime I of FIG. 15, the effect of drawing is approximately reversible in as much as cessation of drawing and continued heating allows for the relaxation of orientation (i.e. a reduction in the index of refraction differences in the three principal material directions) with minimal crystallization. The reversibility is not necessarily complete because Regime I typically appears in a temperature region of large supercooling. Thus crystallization is thermodynamically favored but kinetically hampered. Accumulated time during drawing and relaxation at these temperatures (e.g. via cycling) may eventually bring the material into Regime II via the relatively slow accumulation of crystallinity. Nevertheless, it is this approximate reversibility that distinguishes Regime I from Regime II. In general, the degree of crystallinity (or total polarizability as described later) tolerable in this regime depends on the particular polymer, its quenching conditions and its pre-drawing post process conditions.

The draw ratio at which the rate of crystallization of the birefringent material in the multilayer optical film begins to increase significantly and move into Regime II can be influenced by a number of factors including draw rate, temperature, etc. After the birefringent material has experienced sufficient strain-induced crystallization to enter Regime II, however, it will typically follow the crystallization curve defined by that initial drawing. In other words, the film cannot continue to be drawn without inducing crystallization in the birefringent materials at the increased rates associated with Regime II in the graph of FIG. 15. As a result, the characteristics of the film will be subject to less variability when drawn further in post-forming processes because the crystallization rate of the birefringent materials is, in large part, set by the pre-stretching required to put the film into Regime II.

For a multilayer optical film including birefringent materials that have not experienced sufficient strain-induced crystallization to enter Regime II, further stretching or drawing during post-forming will not be as predictable because the point at which the crystallization rate starts to increase significantly is subject to the factors listed above, e.g., temperature and draw rate. As a result, the film could experience small increases in the draw ratio that result in significant increases in the rate of crystallization of the birefringent materials or it could experience large draw ratios with a relatively small increase in the rate of crystallization of the birefringent materials. In either case, the level of predictability is reduced as compared to a film that includes sufficient strain-induced crystallization such that its rate of crystallization is largely set, i.e., the birefringent materials in the multilayer optical film have entered Regime II.

Figure 15A:
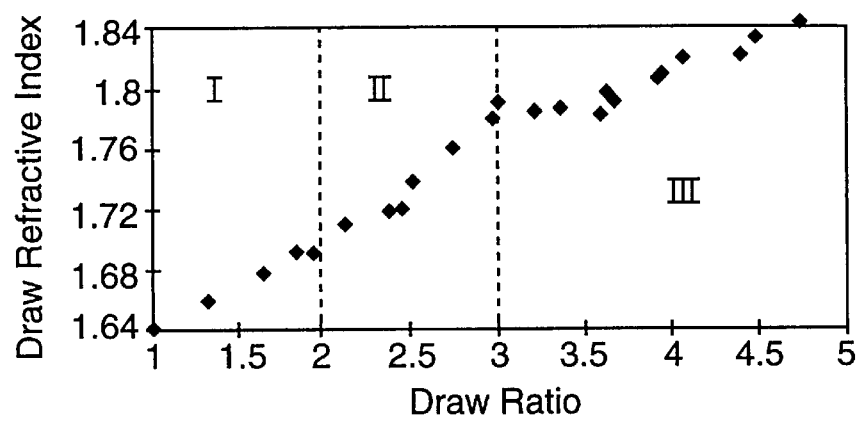
FIG. 15A illustrates the index of refraction in the direction of drawing (vertical axis) as a function of the draw ratio (horizontal axis) for one uniaxially drawn PEN film in which the orthogonal in-plane axis dimension is held generally constant.

In the case of many polymers, especially the polyesters including PEN, PET and copolymers including PEN and/or PET, a third regime develops in which the index of refraction increases at a much slower rate with respect to the draw ratio. Often the total polarizability will also change at a much slower rate as well. FIG. 15A illustrates the index of refraction in the direction of drawing (vertical axis) as a function of the measured draw ratio (horizontal axis) for one uniaxially drawn PEN film in which the orthogonal in-plane axis dimension is held generally constant. The PEN used for this illustrative case had an intrinsic viscosity of 0.48 and was drawn according to a linear draw profile of 20% per second initial draw rate at 130 degrees Celsius.

For the illustrated case, Regime II begins at a draw ratio of about two (2) and Regime III begins at a draw ratio of about three (3). The onset of these regimes depends on process and material conditions including, for example, raising the strain rate, raising the intrinsic viscosity, lowering the temperature, and/or lowering the glass transition temperature (e.g., by lowering the moisture and/or plasticizer content) may all lower the draw ratio at onset for Regimes II and III from those illustrated in FIG. 15A. The molecular weight distribution, rather than just an intrinsic viscosity may also alter the regime onsets. Analogous results can be expected for biaxially drawn films.

In view of the above discussion, one difference between a fully drawn multilayer optical film and an underdrawn multilayer optical film of the same construction is that the fully drawn multilayer optical film includes birefringent materials in which the crystallinity is higher than the crystallinity of the birefringent materials in the underdrawn multilayer optical films. Where the birefringent material in the multilayer optical film is a polyester, it may be preferred that the crystallinity of the birefringent polymer is about 18% or less, more preferably about 15% or less. In comparison, the crystallinity of the same birefringent polyesters in the fully drawn multilayer optical films will be at least about 20% or more, more typically about 25% or more.

In addition to an upper limit for crystallinity, underdrawn films can also be characterized by a lower limit for the crystallinity of the birefringent materials in the underdrawn multilayer optical film, because the birefringent materials in the films do preferably exhibit some level of strain-induced crystallinity. In other words, it is preferred that the birefringent materials in the multilayer optical films have entered Regime II as discussed above. For multilayer optical films including polyesters as the birefringent materials, it may be preferred that the lower limit of crystallinity of the birefringent materials in the multilayer optical film be at least about 3% or more, in some instances more preferably at least about 5% or more, and in other instances even more preferably at least about 10% or more. Higher levels of crystallinity typically provide higher levels of birefringence in the underdrawn state and reflect the degree of underdrawing. Higher birefringence can improve the performance of the initial underdrawn state in a finished post-formed article.

Although we do not wish to be limited by any particular theory, it is believed that the lowest levels of crystallinity provide a minimum level of connectivity between the microcrystalline domains, e.g., via tie chains, which substantially reduces the propensity for large scale relaxation of the developing morphology. In many instances, crystallization at these levels will move the birefringent materials in the multilayer optical film into Regime II. The exact threshold of lower crystallinity depends upon the chemical nature of the material including the composition and molecular weight as well as upon the process conditions such as temperature, rate and duration of draw and heating Although crystallinity may be used to characterize underdrawn multilayer optical films, underdrawn multilayer optical films may alternatively be characterized using what will be referred to herein as "total polarizability" of the layers including birefringent materials. Determination of total polarizability is based on the refractive indices of the layer or layers including birefringent materials within the multilayer optical film.

The "total polarizability difference" will be defined as the difference between the total polarizability of the drawn material and that of the quenched amorphous state of the same material. Any given material is expected to possess a maximum total polarizability difference in a certain maximal fully drawn state. Where the multilayer optical film includes two or more different layers with different compositions of birefringent materials, total polarizability difference will preferably be measured for the layers including birefringent materials with the largest total polarizability difference relative to its maximum total polarizability difference as determined by the methods discussed below.

Refractive indices may be measured by a variety of standard methods using, e.g., an Abbe refractometer or a prism coupling device (e.g. as available from Metricon, Piscataway, N.J.). Although it is difficult to directly measure the refractive indices of the materials in the individual layers of the optical stack of the multilayer optical film, the refractive indices of the optical stack as a whole can be reliably measured. Furthermore, the refractive indices of the optical stack as a whole are weighted averages of the refractive indices of the materials in each of the individual layers making up the optical stack.

If, for example, the optical stack is constructed of two or more materials, the interdiffusional effects between layers are small, and the refractive indices of only one of the materials changes significantly in response to drawing, then the refractive indices of the individual layers can be estimated based on the refractive indices of the optical stack as a whole. These estimates are based on the typically accepted assumption that the refractive indices of the optical stack as a whole are the optical-thickness-weighted averages of the refractive indices of the materials in the various layers of the optical stack.

In another variation, in those films in which one or more of the materials making up the layers of the optical stack are also present in thicker skin layers and/or internal protective boundary layers, then it can typically be assumed that the refractive indices are the same for the same material, whether that material is found in the layers of the optical stack or elsewhere in the multilayer optical film. As a result, if the refractive indices of only one of the materials making up the optical stack is unknown and the refractive indices of the other materials in the optical stack are known, then measurement of the refractive indices of the optical stack will allow for calculation of the refractive indices of the unknown material. In some instances, measurement of the refractive indices may require destructive peeling or other known techniques of isolating the various layers of the multilayer optical films.

Typically, the refractive indices of the birefringent materials in the multilayer optical film will be determined based on the above techniques because it is the refractive indices of the birefringent materials that change in response to drawing or deformation. Assuming conservation of molecular polarizability within the birefringent materials of the optical stack (an assumption that is typically considered a reasonable approximation for many semi-crystalline polymers, including the polyesters used in preferred underdrawn multilayer optical films, e.g., PEN, PET and copolymers of PET and PEN), an anisotropic analogue of the Clausius-Mossetti equation using a Lorenz-Lorentz local field yields the following equation which results in a number referred to above as the total polarizability of the birefringent materials:

$$(n_1^2-1)/(n_1^2+2)+(n_2^2-1)/(n_2^2+2)+(n_3^2-1)/(n_3^2+2)=\rho K=\text{Total polarizability}$$

where $n_1$, $n_2$ and $n_3$ are the refractive indices in the principal directions of a given layer within the multilayer optical film, p is the density of the materials in that layer, and K is a volume polarizability per unit mass for the materials in that layer. Total polarizability is a function of wavelength due to the wavelength dependence of the indices of refraction. As a result, when referred to numerically herein, total polarizability will be determined with respect to light having a wavelength of 632.8 nanometers (e.g., as provided by a helium neon laser light source).

It should be noted that an alternative to the total polarizability equation can also be used. In this alternative, each of the three principal indices in the equation is set equal to the simple average of the three measured principal indices. The total polarizability is then called a refractivity and an analogous refractivity difference may be defined. Likewise, density and crystallinity may be calculated. These may vary from that calculated using the total polarizability. For discussion purposes, the total polarizability calculation is used in the examples that follow. Many semi-crystalline polymers, such as isotactic polypropylene and polybutylene terephthalate, are difficult to quench in the amorphous state; or if quenched, are difficult to re-heat fast enough or process cold enough to prevent significant quiescent crystallization prior to drawing. Such polymers may not exhibit Regime I under typical process conditions. Rather, the connectivity in the morphology means that all subsequent drawing is at least partially effective and the material essentially begins in Regime II after casting and quenching. As with materials that exhibit Regime I behavior, these materials can still be drawn and oriented. Moreover, the higher the degree of underdrawing (i.e. the lower the degree of drawing), the higher the level of residual extensibility available during the post processing (e.g. thermoforming).

From a functional standpoint, the onset of Regime II sets a certain level of extensibility related to the ultimate extensibility. This ultimate extensibility will vary somewhat with draw conditions. The amount of underdrawing is relative to this ultimate extensibility. Fully drawn films are drawn near to this limit. Underdrawn films are drawn below this amount, but preferably have been drawn past the onset of Regime II. The level of underdrawing desired may be a function of the level of extensibility desired for the subsequent post forming process.

The level of underdrawing is also a function of direction. Upon onset of Regime II, a certain level of drawing is locked in. This amount may vary in direction depending upon the process conditions at the time of onset. For example, a uniaxially drawn film will have a higher degree of underdrawing in the non-drawn direction at the point of Regime II onset. In the case of mirror films, equal underdrawing in both directions may be preferred. This may be achieved by minimizing the in-plane birefringence. As used here, the in-plane birefringence is simply defined as the absolute value or magnitude of the difference between the maximum and minimum refractive index values in the plane on the film. In the case of a uniaxially drawn film, this is typically the difference between the indices of refraction in the draw and non-drawn directions. In the case of polarizing films, a large in-plane birefringence is desired within the constraints of the underdrawing required to obtain a desired level of extensibility in the post process.

As can be seen by the directional nature of underdrawing, crystallinity or total polarizability alone does not fully characterize the level of underdrawing, although it sets useful limits with regards to the transition between Regime I and II and between underdrawn and fully drawn films. It should be understood that a certain level of extensibility reflects a corresponding level of underdrawing. For example, films drawn quickly in Regime II may not achieve the same level of crystallinity as those drawn slowly or those that continue to be heated at the draw temperature after drawing to heat set the films. The latter may be less extensible than the former; however, they may still be more extensible than other films slightly more drawn but less heat set. Thus maximum and minimum levels of crystallinity and/or total polarizability difference are most applicable in delineating the bounds of what is meant as an underdrawn film and not necessarily a sole measure of the relative performance among that class of films.

The total polarizability difference of the birefringent materials in underdrawn multilayer optical films including PEN (and, by the definitions provided below in the section regarding materials selection, predominantly PEN copolymers) as measured in the birefringent layers is preferably within a range of from about 0.002 up to about 0.018, more preferably within a range of from about 0.002 up to about 0.016. Within either range, it may be desirable that the maximum in-plane birefringence of reflective polarizing multilayer optical films is less than about 0.22, more preferably less than about 0.17, and, in some cases, still more preferably less than about 0.15. In the case of underdrawn mirror films, a maximum in-plane birefringence of less than about 0.14 is preferred in combination with either of the ranges for the total polarizability difference in the birefringent materials.

Total polarizability difference of the birefringent materials in underdrawn multilayer optical films including PET (and, by the definitions provided below in the section regarding materials selection, predominantly PET copolymers) as the measured birefringent layer is preferably within a range of from about 0.002 up to about 0.030, more preferably within a range of from about 0.002 up to about 0.0024. In the case of mirror films, these ranges are preferably coupled with a maximum in-plane birefringence of less than about 0.11, more preferably less than about 0.04.

The differences between the preferred levels of total polarizability and birefringence for the various polymers reflects the differences in the amorphous and crystalline densities of the different materials. The differences also reflect the intrinsic maximum birefringence of the different polymers, as well as the limits of extensibility after the onset of Regime II as discussed above.

In addition to the total polarizability and maximum in-plane birefringence, underdrawn multilayer optical films can also be characterized by reflectivity. For example, where the total polarizability difference of the measured birefringent materials is within the various ranges discussed above, it may be preferred that the multilayer optical film reflect at least about 85% of normal incident light of desired wavelengths that is polarized along at least one in-plane axis, more preferably the film may reflect at least about 90% of normal incident light of desired wavelengths that is polarized along at least one in-plane axis. If the multilayer optical film is intended to be a mirror film, i.e., not a reflective polarizer, it may be preferred that the reflective performance of the film in terms of percent reflectance hold for at least one in-plane axis, more preferably two generally perpendicular in-plane axes.

As indicated in the equation presented above, total polarizability of the material(s) in a given layer of the optical stack of the multilayer optical film represents the product of density and the volume polarizability per unit mass of the material(s) in that layer. The volume polarizability per unit mass (K) is typically considered an invariant material property under draw according to the conservation of molecular polarizability assumption discussed above. Drawing of birefringent materials causes strain-induced crystallization as discussed above and, in most birefringent materials, the density of the material varies based on whether the material is crystallized or amorphous.

As a result, the density of the birefringent materials in the multilayer optical films changes based on the amount of strain-induced crystallization in the birefringent materials. Those changes in density can be used to estimate the level of strain-induced crystallization in the underdrawn multilayer optical films according to the present invention. This method of determining the level of strain-induced crystallization is not, however, without its limits.

One class or type of preferred birefringent materials used in the multilayer optical films according to the present invention are semi-crystalline. If the crystals in the semi-crystalline birefringent materials are relatively small, an effective refractive index for the semi-crystalline aggregate may be measured. This is often the case in polymers, such as polyesters (e.g., PEN and PET), that are drawn from a relatively amorphous state to a state of semi-crystallinity. In such cases, the density of the birefringent material (based on the refractive indices) may be estimated from the total polarizability and used to determine the level of crystallinity in the birefringent materials using a standard correlation between crystallinity and density.

In either case, the above discussions set out different approaches to characterizing underdrawn films according to the present invention. In the first, the strain-induced crystallinity of the birefringent materials is measured and used to define underdrawn multilayer optical films. In the second, the refractive indices of the birefringent materials can be used to determine the total polarizability of the birefringent materials which can also be used to define underdrawn multilayer optical films. In still another manner, the strain-induced crystallinity can be determined based, at least in part, on the refractive indices used to determine total polarizability.

For example, the total polarizabilities of amorphous cast webs of PET and PEN are found to be about 0.989 and 1.083, respectively, and the densities of the amorphous materials are measured using a standard density gradient column at about 1.336 and 1.329 grams per cubic centimeter, respectively. The resulting volume polarizabilities can be calculated at about 0.740 and 0.815 cubic centimeters per gram for PET and PEN, respectively. Densities of drawn films of PET and PEN may now be calculated by dividing the total polarizabilities by the respective volume polarizabilities. Moreover, the crystallinity may be estimated given the density of the pure crystalline phase, estimated as 1.407 grams per cubic centimeter for the typical crystalline phase of PEN and 1.455 grams per cubic centimeter for the crystalline PET.

The crystallinity can be estimated via a linear interpolation of the actual density between the amorphous density (zero crystallinity) and the pure crystalline density. Such crystalline estimates may vary from other measures as it neglects densification of the non-crystalline phase due to orientation and rarefication of the crystalline phase due to imperfections and defects. Other methods for determining crystallinity include Differential Scanning Calorimetry and X-ray Scattering. Measurements obtained by these methods may be correlated to the density or total polarizability methods described herein through the use of suitable drawn film standards. It can typically be assumed that copolymers will have volume polarizabilities that are weight averages of their components, so that similar calculations can be made on co-polymers, if the type of crystals are known. Usually, this is the crystal corresponding to the predominant crystallizing monomer or subunit. Total polarizability can be used to characterize the underdrawn state of many systems. However, lack of a definitive total polarizability measurement in no way limits the utility of the invention. In some cases, the extensibility of a non-birefringent layer may be limiting. For example, a non-birefringent semi-crystalline second material layer may still become drawn during film processing. Under drawing to suit this layer would be desirable When the material has very low or no inherent birefringence, as is the case with a few polymers such as poly methyl methacrylate, then little or no orientational information can be derived. Nevertheless, the extensibility of such a non-birefringent non-crystalline second material may also be limiting. In the case of non-crystalline materials, the orientation may be relaxed and thus the extensibility recovered by pre-heating prior to draw. Optimizing the conditions of such pre-heating must balance the recovered extensibility of the amorphous material against any lost extensibility by the birefringent semi-crystalline first material. In the examples that follow below, it is believed that the birefringent strain-hardening layers (e.g., PEN or 90/10 coPEN layers) are the limiting layers for extensibility, whereas the second material layers (e.g., PMMA, PETG, or 70/0/30 coPEN) are believed to be nearly isotropic for the conditions used to manufacture the optical stacks. Finally, in a semi-crystalline material, if the crystals are relatively large, haze and scattering may obscure index measurements.

Process Conditions for Post-forming Multilayer Optical Films

Because the post-formed multilayer optical films used in connection with the present invention rely on birefringent materials that provide strain-induced refractive index differentials to obtain the desired optical properties, variations in deformation of the multilayer optical film during post-forming can be particularly problematic.

As discussed above, the index of refraction differentials ($\Delta x$, $\Delta y$) in the multilayer optical film as manufactured are, in large part, the result of drawing of the multilayer optical film during manufacturing which causes the indices of refraction of the birefringent materials to change. Those changes cause refractive index differentials large enough to provide the desired reflective properties. Because the strain in the multilayer optical film during manufacturing is largely uniform, the strain-induced index of refraction differentials are also largely uniform over the film, and the resulting reflective properties are also largely uniform.

In post-forming processes the birefringent layers in the multilayer optical film are subjected to additional strain. One difference from manufacturing of the multilayer optical film is, however, that the strain induced during post-forming is not uniform over the film. The variations in thickness of the optical stack in a post-formed multilayer optical film as discussed above are, in part, indicative of the variations in strain over the post-formed multilayer optical film.

As a result, if the birefringent materials in the multilayer optical film are capable of further strain-induced index of refraction changes, the index of refraction differentials in the multilayer optical film may be changed as a result of post-forming. Furthermore, if the strain induced during post-forming is not uniform, the index of refraction changes in the post-formed multilayer optical film may also be non-uniform and may result in non-uniform optical properties in the post-formed multilayer optical film.

In addition to non-uniform post-forming strain-induced changes, another difficulty associated with post-forming multilayer optical films including strain-induced refractive index differentials in connection with birefringent materials is that many post-forming processes employ heat to improve the working properties of the multilayer optical film during deformation. The strain-induced changes in the refractive indices of the birefringent materials in the multilayer optical film are typically the result of strain-induced crystallization of the birefringent materials. The strain-induced crystallization and corresponding refractive indices can, however, be changed when the birefringent materials are subjected to heat during post-forming.

For example, heating may result in increased crystallization due to the heat during post-forming or decreased crystallization as a result of melting or relaxation during post-forming. In either case, changes in the crystallization level of the birefringent materials can result in a change in the refractive index differentials in the film. The potential crystallization changes in the birefringent materials may be further exacerbated by the simultaneous post-forming deformation and heating of the film which, in combination, may cause greater changes in the recrystallization/refractive index of the birefringent materials than either action alone.

The present invention, however, overcomes these difficulties to provide articles including post-formed multilayer optical film and methods of producing those articles. These results are achieved even though all of the multilayer optical films referred to in connection with the present invention include birefringent materials and rely on strain-induced refractive index differentials to obtain the desired optical properties.

Although post-forming may be most advantageously pursued using the "underdrawn" multilayer optical films described herein, it may also be possible to obtain desirable post-forming results using multilayer optical films including a birefringent material and other materials that do not meet the definitions of underdrawn multilayer optical films, e.g., constructed according to U.S. Pat. No. 08/472,241.

In the post-forming methods of the present invention, it may be desirable to heat the multilayer optical films to forming temperatures that are near to, but below, the peak crystalline melting temperatures of the birefringent materials. Such heating can improve the extensibility of multilayer optical films during post-forming processing. By heating the multilayer optical film to those levels, the tendency of the multilayer optical film to fracture or tear at a given draw ratio during post-forming may be decreased. In addition, the forces required to post-form the films may be reduced as a result of the increased forming temperature.

Underdrawn multilayer optical films may also have increased extensibility under these process conditions. Because processing under these conditions is in the melting regime, precise temperature control is desirable to ensure uniform drawing and reduce or prevent damage to the post-formed multilayer optical film in the article. Such damage could take the form of complete melting, with concomitant loss of birefringence and/or hole formation in the multilayer optical film.

Reducing the stress required for a given amount of deformation during post-forming may reduce the tendency of the materials in the film to fracture, thereby enhancing extensibility. Heating the multilayer optical film to a forming temperature near the peak crystalline melting temperature of the birefringent material in the film may also enhance extensibility by melting less perfect crystals, thereby loosening the morphological microstructure in the birefringent material layers.

For example, one material used in some preferred multilayer optical films according to the present invention is polyethylene naphthalate (PEN), which has a peak melting point of about 270 degrees Celsius (520 degrees Fahrenheit) using standard differential scanning calorimetry (DSC). The onset of melting is, however, often seen at about 255 degrees Celsius (490 degrees Fahrenheit) or below. This onset of melting may be attributable to the melting of less well-developed crystals within the PEN with the peak melting temperature being that point at which all or nearly all of the crystals in the material have melted. Heating the birefringent materials in the multilayer optical film may also increase mobility within the microstructure, thereby activating crystal slip and other deformation mechanisms that could enhance extensibility of the multilayer optical film.

The extent to which heating may improve extensibility of the multilayer optical films according to the present invention will, at least in part, vary based on the materials used in the films. Some materials may exhibit larger increases in extensibility when heated as compared to others. Furthermore, the combination of materials within each of the multilayer optical films according to the present invention can also affect improvements in extensibility of the film as a whole.

For example, to improve the extensibility of the multilayer optical films, it may be preferred to heat the multilayer optical films to a forming temperature in the range of from about 30 degrees Celsius (about 55 degrees Fahrenheit) below the peak crystalline melting temperature of the birefringent material up to about the peak crystalline melting temperature of the birefringent material during post-forming. It may be more preferred to heat the film to a forming temperature in the range of from about 15 degrees Celsius (about 30 degrees Fahrenheit) below the eak crystalline melting temperature of the birefringent material up to about the eak crystalline melting temperature of the birefringent material during post-forming. These forming temperatures may increase extensibility and reduce the likelihood of fracture of multilayer optical films during post-forming processing.

A way to improve uniformity in the multilayer optical film during post-forming is to include materials in the multilayer optical film that are subject to strain hardening during deformation. Strain hardening is a property of materials in which the stress required to achieve a particular level of strain increases as the material is strained (i.e., stretched). Essentially, strain hardening materials may provide self-regulation of the thinning process due to post-forming.

In terms of molding, as the multilayer optical film is stretched during post-forming, unquenched sections of the film that have not yet made contact with a mold surface will tend to draw more uniformly after the onset of strain hardening. As a result, those portions of the film that have been stretched to the point at which strain hardening occurs will progressively stretch less while those portions of the film that have not experienced strain hardening will continue to stretch at faster rates. The end result is that the thinner (i.e., strain hardened) portions of the film will thin to a certain point after which the thicker portions of the film will continue to stretch and become thinner, effectively evening out the stretching or thinning of layers in the multilayer optical film during post-forming processing. This reinforcement effect of strain hardening is also operative in post-forming processes in which no mold is present to provide quenching of the film during post-forming. One material that provides strain hardening properties in a multilayer optical film is PEN. In general, strain-hardening is typically observed in many semi-crystalline polymers at high enough levels of strain.

Strain-hardening can help to regulate the uniformity of the drawing process, thus potentially reducing variations in the amount of deformation experienced by the film during post-forming. If the bandwidth of the multilayer optical film as manufactured is specifically designed to the final biaxial draw ratio of the post-forming process, rather than the draw ratio at tear or fracture as discussed above, then strain hardening can allow the design of a multilayer optical film with a narrower, more reflective band for use in the post-forming process.

The effect of strain hardening may also influence the degree to which vacuum-forming as one post-forming process will allow for adequate or desirable mold replication. Pressurized or plug assisted molding techniques may be needed for accurate post-forming processing of materials in which strain hardening potentially increases the resistance of the film to stretching during the molding process. The effect of strain hardening may be influenced by both the post-forming draw conditions and the degree of draw (strain-hardening) before post-forming is initiated.

Figure 16:
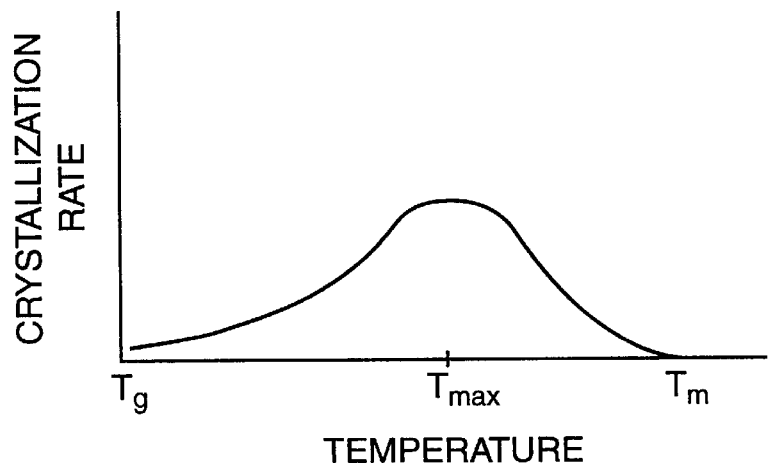
FIG. 16 is a graph illustrating temperature (horizontal axis) versus crystallization rate (vertical axis) for an exemplary birefringent material.

In addition to the above, one further consideration in developing an appropriate post-forming process may include an analysis of the rate of crystallization for the given materials as a function of temperature. Referring now to FIG. 16, an idealized graph of rate of crystallization (vertical axis) as a function of temperature (horizontal axis), it can be seen that crystallization rate increases with temperature to a certain point, referred to as the peak crystallization rate temperature $T_{max}$, after which the rate of crystallization tends to fall again as the temperature moves towards the peak crystalline melting temperature $T_m$ of the material. Differential scanning calorimetry may be used to estimate $T_{max}$. For PEN, $T_{max}$ has been estimated at about 220 degrees Celsius (about 430 degrees Fahrenheit) using differential scanning calorimetry upon heating at 20° C./min., and $T_{max}$ has been estimated at about 208 degrees Celsius (about 406 degrees Fahrenheit) using differential scanning calorimetry upon cooling at 5° C./min. Although we do not wish to be held to any theory, it is thought that the extensibility of multilayer optical films during post-forming can be improved in many cases if the forming temperatures used are not the same as the peak crystallization rate temperature of the birefringent material or materials in the film. This may be particularly applicable to films that have not already been heat set, and especially underdrawn films. Nevertheless, if the film is sufficiently underdrawn, extensibility and thus post-processability may still be acceptable after heating at these temperatures. The following discussion elucidates the effects of post forming near $T_{max}$ for some cases; e.g. certain underdrawn, non-heatset films comprising certain polyesters. It should be understood that multilayer optical films comprising materials other than polyesters may behave differently in their relation between peak crystallization temperature and optimal forming temperatures.

Further crystallization and morphological changes during pre-heating before post-forming may reduce extensibility and post-formability. In one aspect, it may be preferred that the forming temperature of the film during post forming be lower than the peak crystallization rate temperature of the birefringent material with the lowest peak crystallization rate temperature in the film, more preferably more than about 10 degrees Celsius below the peak crystallization rate temperature of the birefringent material with the lowest peak crystallization rate temperature in the film, and even more preferably more than about 20 degrees Celsius below the peak crystallization rate temperature of the birefringent material with the lowest peak crystallization rate temperature in the film. It may also be preferred that the forming temperature be greater than the peak crystallization rate temperature of the birefringent material with the highest peak crystallization rate temperature in the film, more preferably more than about 10 degrees Celsius above the peak crystallization rate temperature of the birefringent material with the highest peak crystallization rate temperature in the film, and even more preferably about 20 degrees Celsius above the peak crystallization rate temperature of the birefringent material with the highest peak crystallization rate temperature in the film.

These forming temperature limitations may be combined as desired. For example, it may be preferred that the forming temperature be more than about 10 degrees Celsius below the peak crystallization rate temperature of the birefringent material with the lowest peak crystallization rate temperature in the film or more than about 20 degrees Celsius above the peak crystallization rate temperature of the birefringent material with the highest peak crystallization rate temperature in the film. In another alternative, it may be desired that the forming temperature be more than about 20 degrees Celsius below the peak crystallization rate temperature of the birefringent material with the lowest peak crystallization rate temperature in the film or greater than the peak crystallization rate temperature of the birefringent material with the highest peak crystallization rate temperature in the film. Other combinations of these different limitations will also be apparent upon further analysis.

Where only one birefringent material is present in the multilayer optical film, the forming temperature limitations can be more simply expressed. It may be preferred that the forming temperature of the film be different than the peak crystallization rate temperature of the birefringent material in the film. Alternatively, it may be preferred to define the forming temperature in terms of ranges, e.g., it may be preferred that the forming temperature of the film be more than about 10 degrees Celsius below the peak crystallization rate temperature of the birefringent material, more preferably more than about 20 degrees Celsius below the peak crystallization rate temperature of the birefringent material in the film. It may also be preferred that the forming temperature be more than about 10 degrees Celsius above the peak crystallization rate temperature of the birefringent material film, more preferably about 20 degrees Celsius above the peak crystallization rate temperature of the birefringent material in the film.

After post-forming draw, it may be desirable to deliberately heat set the formed article to improve its reflectivity. This heat setting preferably follows the last post-forming drawing step; e.g., further crystallization can now be encouraged with attendant refractive index difference increases without consideration of further extensibility after the final post-forming draw step.

Although the methods of post-forming multilayer optical films in general are discussed above, the post-forming of underdrawn multilayer optical films may be varied while still providing desirable post-forming results. One significant variation is that the forming temperature of the underdrawn multilayer optical films may lie well below the peak crystallization rate temperatures of the birefringent materials within the films. Heat setting following the final post-forming draw step may also be desirable for articles manufactured from underdrawn multilayer optical films. For example, the crystallinity (and, as a result, the reflectance) of portions of the underdrawn films that have not been drawn during post-forming can be increased by heat-setting following the final post-forming draw steps. In addition, those portions of the underdrawn film that were drawn during post-forming can also experience increased crystallinity and the attendant reflectance.

The underdrawn multilayer optical films can be provided with and post-formed according to all of the variations described above with respect to multilayer optical films in general. In other words, they can be provided as highly reflective films that retain their reflectivity after post-forming, etc. Furthermore, the modifications discussed above for thinning effects should also be considered when manufacturing and processing underdrawn multilayer optical films as well.

Post-Forming Selected Areas of Multilayer Optical Films

The dental articles including post-formed multilayer optical film and the methods of post-forming multilayer optical film described thus far have focused on dental articles and methods in which the post-formed multilayer optical film exhibits uniform optical properties. It may, however, be desirable to provide dental articles and methods according to the present invention in which the post-formed multilayer optical film exhibits non-uniform appearances. For example, it may be desired to provide post-formed multilayer optical film in which selected areas of the multilayer optical film are reflective for light of desired wavelengths while other selected areas of the post-formed multilayer optical film transmit light with the same or other desired wavelengths.

It may also be desirable to provide an article including post-formed multilayer optical film in which selected areas in the post-formed multilayer optical film are transmissive for visible wavelengths while the remainder of the post-formed multilayer optical film is reflective for visible wavelengths. To accomplish that result using a multilayer optical film that is, as manufactured, reflective for visible light, the multilayer optical film in the selected areas could be stretched or thinned during the post-forming process such that all of the tuned bandwidths of the layers in the multilayer optical film stack in the selected transmissive areas are less than 400 nanometers after post-forming. The result of such a process would be an article including post-formed multilayer optical film that is highly reflective in the areas in which the reflective bandwidth remains in the visible spectrum, while the article would exhibit transmission in those areas in which the post-formed multilayer optical film has been thinned to allow transmission in the visible spectrum.

As an alternative to the previously described process, multilayer optical films could be provided and post-formed in methods that result in selected transmissive and reflective areas within the post-formed multilayer optical film in the same article, but in which the unthinned layers remain transparent while those selected areas that are thinned during post-forming become reflective. For example, the multilayer optical film as manufactured could be tuned to be reflective for wavelengths from about 900 to about 2025 nanometers, i.e., above the visible spectrum. Films designed to reduce higher order harmonics that give perceptible color in the visible region of the spectrum may be preferred. Some suitable films are described in U.S. Pat. Nos. Re. 34,605 and 5,360,659, and in U.S. patent application Ser. No. 09/006,118.

If such a multilayer optical film were post-formed, the selected areas of the multilayer optical film that are to be reflective would be deliberately thinned during post-forming by an appropriate factor, e.g., 2.25, to retune the multilayer optical film in those selected areas such that visible wavelengths, i.e., those between about 400 to about 900 nanometers, were substantially reflected. The remaining portions or areas of the multilayer optical film and the article that are not thinned sufficiently to reflect light in the visible spectrum would remain transmissive to visible light.

Many variations on these concepts can be envisioned. For example, the multilayer optical films could be post-formed in methods such that the selected areas are sharply defined resulting in short transition zones between reflective/transparent areas, or they could be deliberately designed with long transition zones in which the post-formed multilayer optical film would exhibit iridescence as various wavelengths of light were reflected or transmitted. In another variation, different selected areas could be thinned to reflect different selected wavelengths. In that manner, the selected areas could exhibit, e.g., different colors. The end result of applying the principles of multilayer optical films and methods of post-forming multilayer optical films according to the present invention is that desired combinations of optical effects can be obtained by selecting films with the desired optical and post-forming properties and processing the films to obtain post-formed articles with the desired optical properties.

Figure 17:
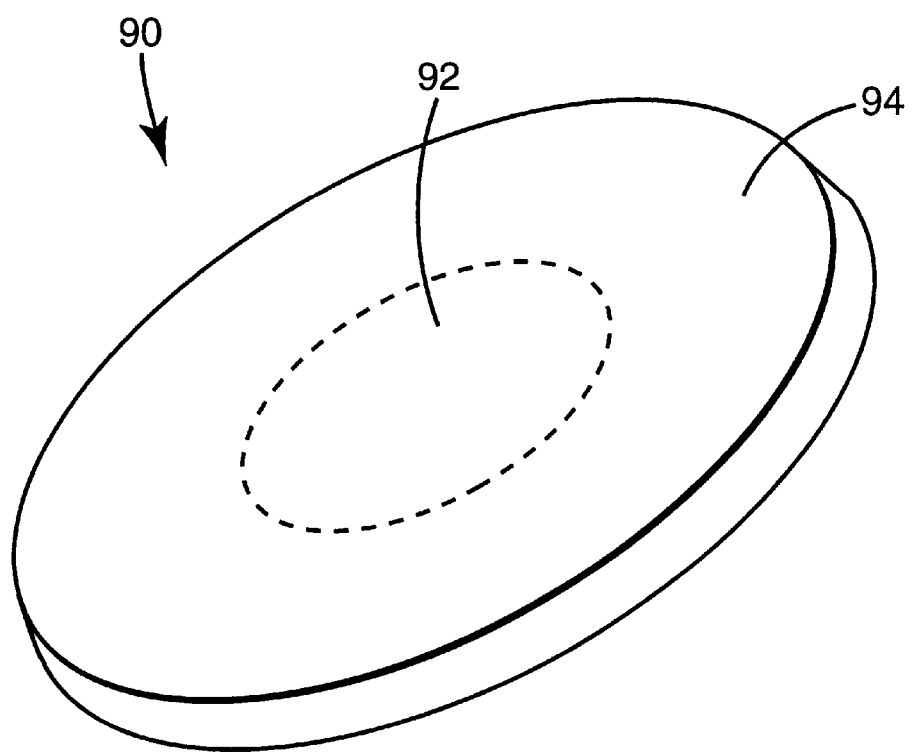
FIG. 17 is a perspective view of an article including post-formed multilayer optical film with areas having different optical properties.

One example of an article including post-formed multilayer optical film that is deformed in selected areas is depicted in FIG. 17. The article 90 may be, e.g., the optical surface of a dental mirror in which a first area 92 of the article 90 is transmissive for selected wavelengths of light while a second area 94 of the article 90 is reflective for different selected wavelengths of light. The multilayer optical film can be post-formed in manners such as those described above such that the multilayer optical film in the second area 94 surrounding the first area 92 is thinned during post-forming such that the multilayer optical film in the second area 94 is transparent to at least a portion of the visible spectrum while the first area 92 is substantially unchanged.

In another embodiment, the second area 94 may be maintained as reflective to the visible spectrum while the first area 92 are deformed or thinned to provide a different optical effect from the second area 94. For example, the selected area 92 may be embossed or otherwise post-formed to thin the film in first area 92 sufficiently that it becomes transmissive to at least a portion of the visible spectrum. Other variations on the construction and manufacture of articles including post-formed multilayer optical film in which selected areas are post-formed can also be envisioned based on the examples discussed above.

Post-Forming Multilayer Optical Films with Substrates

Figure 18:
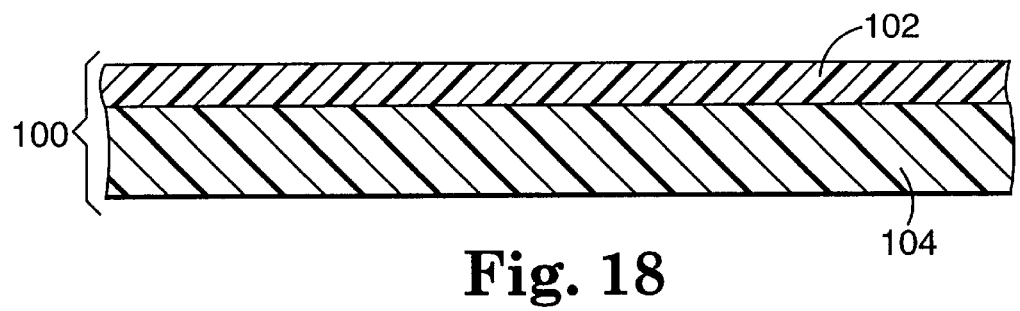
FIG. 18 is a cross-sectional view of a composite including an multilayer optical film and a substrate.

FIG. 18 illustrates another feature of multilayer optical films and articles including post-formed multilayer optical films according to the present invention. In some instances the post-formed multilayer optical films alone may lack sufficient body or rigidity to provide the desired mechanical properties. For example, the multilayer optical films may lack sufficient structural strength and/or stiffness to hold a desired shape. FIG. 18 illustrates one solution to that problem in that the multilayer optical film 102 may be laminated to or otherwise attached to a substrate 104 to provide a composite 100 with the desired mechanical properties. In some instances, the substrate 104 may be manufactured integrally with the multilayer optical film 102, and in other cases the multilayer optical film 102 may be manufactured independently and later attached to the substrate 104 to form the composite 100. If the substrate 104 is manufactured integrally with the multilayer optical film 102, it may be a thicker layer of one of the materials provided in the multilayer optical film 102 or it may be provided of another material that can be coextruded, cast, or otherwise formed with the multilayer optical film 102. In another alternative, the substrate 104 may be provided as a coating on the multilayer optical film.

Furthermore, although a substrate 104 is shown only one side of the multilayer optical film 102, it will be understood that the substrate 104 could be provided on both sides of the multilayer optical film 102. In addition, although the substrate 104 is depicted as a single layer, it will be understood that it could be a composite of different layers of the same or different materials based on the desired characteristics of the substrate 104

In some cases, the materials selected for the substrate 104 may have little, if any, effect on the optical properties of the multilayer optical film 102 but will provide a post-formable layer that is otherwise compatible with the multilayer optical film 102. In one aspect, the substrate 104 may simply supply desired structural stiffness/rigidity to the post-formed article, thereby reducing the need to laminate the post-formed multilayer optical film to another structure. Examples of suitable materials for the substrate 104 include, but are not limited to polycarbonates, polyvinyl chlorides, PETG, acrylics, methacrylics, nylons, polyolefin, polypropylene, etc.

Another mechanical property that may be supplied by the substrate 104 is strain-hardening during deformation as discussed above with respect to the multilayer optical film. That strain-hardening property may be used to limit the stresses placed on the attached multilayer optical film 102, thereby acting to distribute the stresses over the multilayer optical film 102 in a way that improves the post-formability of the composite 100 over the post-formability of the multilayer optical film 102 alone.

The materials selected for substrate 104 may provide desired optical properties instead of, or in addition to, desired mechanical properties. For example, the substrate 104 may function as a mirror for selected wavelengths of light such as infrared radiation, the substrate 104 may include colorants or otherwise introduce color into the composite 100, the substrate 104 may provide diffusing properties in either or both transmittance or reflectance (to, e.g., reduce iridescence).

Figure 19:
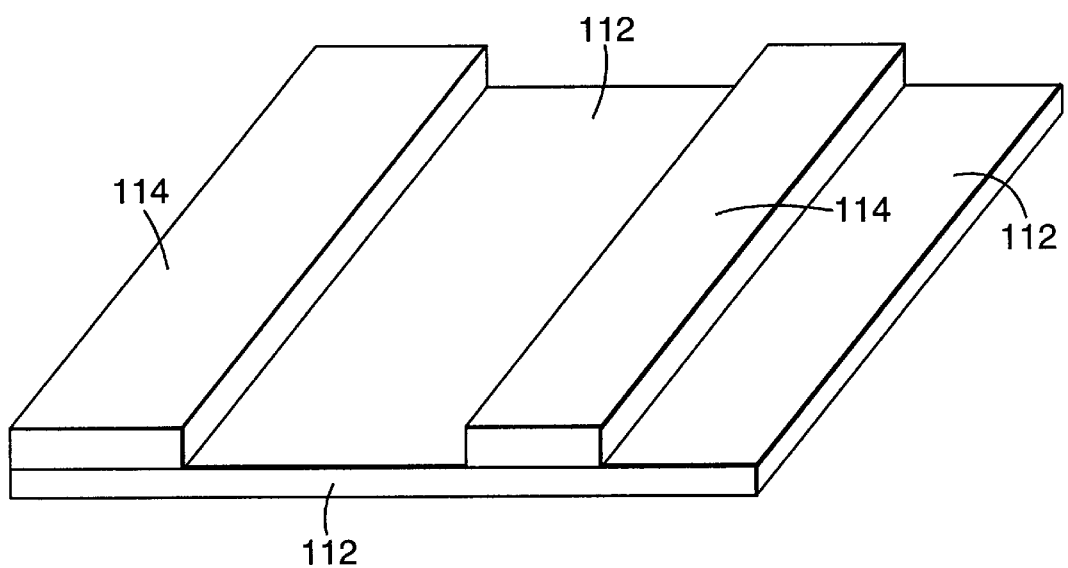
FIG. 19 is a plan view of the composite of FIG. 18 illustrating that the substrate may be provided in selected areas.

Although in many instances the substrate 104 will be coextensive with the multilayer optical film 102, it is also envisioned that the substrate may be attached only on selected areas of the multilayer optical film as depicted in FIG. 19 where the substrate 114 is provided in selected areas on the multilayer optical film 112. It will also be understood that the substrate 114 may be provided in the form of a grid, mesh or other discontinuous form on the multilayer optical film 112 to improve its post-formability. It may, for example, be advantageous to provide the substrate 114 discontinuously in manners that assist in defining the selected areas of the post-formed multilayer optical film as described above with respect to FIG. 17. In such an application, the substrate 114 may prevent or reduce drawing of the multilayer optical film 112 during post-forming in manners that are difficult or impossible to achieve through the use of post-forming techniques alone.

Regardless of whether the multilayer optical films used in connection with the present invention are included with substrates, underdrawn or fully drawn, etc. the selection of the materials in the films is discussed below.

Materials Selection

A variety of polymer materials suitable for use in the present invention have been taught for use in making coextruded multilayer optical films. For example, the polymer materials listed and described in U.S. Pat. Nos. 4,937, 134, 5,103,337, 5,1225,448,404, 5,540,978, and 5,568,316 to Schrenk et al., and in 5,122,905, 5,122,906, and 5,126,880 to Wheatley and Schrenk are useful for making multilayer optical films according to the present invention. Of special interest are birefringent polymers such as those described in U.S. Pat. Nos. 5,486,949 and 5,612,820 to Schrenk et al, U.S. application Ser. No. 08/402,041 to Jonza et al, and U.S. Application entitled "Modified Copolyesters and Improved Multilayer Reflective Films" filed on Jan. 13, 1998 under Attorney Docket No. 53550USA6A. Regarding the preferred materials from which the films are to be made, there are several conditions which should be met to make the multilayer optical films of this invention. First, these films should consist of at least two distinguishable polymers; the number is not limited, and three or more polymers may be advantageously used in particular films. Second, at least one of the two required polymers, referred to below as the first polymer, preferably has a stress optical coefficient having a large absolute value. In other words, it preferably should be capable of developing a large birefringence when stretched. Depending on the application, the birefringence may be developed between two orthogonal directions in the plane of the film, between one or more in-plane directions and the direction perpendicular to the film plane, or a combination of these. In the special case that the isotropic indices are widely separated, the preference for large birefringence in the first polymer may be relaxed, although at least some birefringence is desired. Such special cases may arise in the selection of polymers for mirror films and for polarizer films formed using a biaxial process which draws the film in two orthogonal in-plane directions. Third, the first polymer should be capable of maintaining birefringence after stretching, so that the desired optical properties are imparted to the finished film. Fourth, the other required polymer, referred to as the "second polymer", should be chosen so that in the finished film, its refractive index, in at least one direction, differs significantly from the index of refraction of the first polymer in the same direction. Because polymeric materials are typically dispersive, that is, the refractive indices vary with wavelength, these conditions must be considered in terms of a particular spectral bandwidth of interest.

Other aspects of polymer selection depend on specific applications. For polarizing films, it is often advantageous for the difference in the index of refraction of the first and second polymers in one film-plane direction to differ significantly in the finished film, while the difference in the orthogonal film-plane index is minimized. If the first polymer has a large refractive index when isotropic, and is positively birefringent (that is, its refractive index increases in the direction of stretching), the second polymer will typically be chosen to have a matching refractive index, after processing, in the planar direction orthogonal to the stretching direction, and a refractive index in the direction of stretching which is as low as possible. Conversely, if the first polymer has a small refractive index when isotropic, and is negatively birefringent, the second polymer will typically be chosen to have a matching refractive index, after processing, in the planar direction orthogonal to the stretching direction, and a refractive index in the direction of stretching which is as high as possible.

Alternatively, it is possible to select a first polymer which is positively birefringent and has an intermediate or low refractive index when isotropic, or one which is negatively birefringent and has an intermediate or high refractive index when isotropic. In these cases, the second polymer may typically be chosen so that, after processing, its refractive index will match that of the first polymer in either the stretching direction or the planar direction orthogonal to stretching. Further, the second polymer will typically be chosen such that the difference in index of refraction in the remaining planar direction is maximized, regardless of whether this is best accomplished by a very low or very high index of refraction in that direction.

One means of achieving this combination of planar index matching in one direction and mismatching in the orthogonal direction is to select a first polymer which develops significant birefringence when stretched, and a second polymer which develops little or no birefringence when stretched, and to stretch the resulting film in only one planar direction. Alternatively, the second polymer may be selected from among those which develop birefringence in the sense opposite to that of the first polymer (negative—positive or positive—negative). Another alternative method is to select both first and second polymers which are capable of developing birefringence when stretched, but to stretch in two orthogonal planar directions, selecting process conditions, such as temperatures, stretch rates, post-stretch relaxation, and the like, which result in development of unequal levels of orientation in the two stretching directions for the first polymer, and/or for the second polymer such that one in-plane index is approximately matched to that of the first polymer, and the orthogonal in-plane index is significantly mismatched to that of the first polymer. For example, conditions may be chosen such that the first polymer has a biaxially oriented character in the finished film, while the second polymer has a predominantly uniaxially oriented character in the finished film.

The foregoing is meant to be exemplary, and it will be understood that combinations of these and other techniques may be employed to achieve the polarizing film goal of index mismatch in one in-plane direction and relative index matching in the orthogonal planar direction.

Different considerations apply to a reflective, or mirror, film. Provided that the film is not meant to have some polarizing properties as well, refractive index criteria apply equally to any direction in the film plane, so it is typical for the indices for any given layer in orthogonal in-plane directions to be equal or nearly so. It is advantageous, however, for the film-plane indices of the first polymer to differ as greatly as possible from the film-plane indices of the second polymer. For this reason, if the first polymer has a high index of refraction when isotropic, it is advantageous that it also be positively birefringent. Likewise, if the first polymer has a low index of refraction when isotropic, it is advantageous that it also be negatively birefringent. The second polymer advantageously develops little or no birefringence when stretched, or develops birefringence of the opposite sense (positive—negative or negative—positive), such that its film-plane refractive indices differ as much as possible from those of the first polymer in the finished film. These criteria may be combined appropriately with those listed above for polarizing films if a mirror film is meant to have some degree of polarizing properties as well.

Colored films can be regarded as special cases of mirror and polarizing films. Thus, the same criteria outlined above apply. The perceived color is a result of reflection or polarization over one or more specific bandwidths of the spectrum. The bandwidths over which a multilayer film of the current invention is effective will be determined primarily by the distribution of layer thicknesses employed in the optical stack(s), but consideration must also be given to the wavelength dependence, or dispersion, of the refractive indices of the first and second polymers. It will be understood that the same rules applied to the visible spectrum will also generally be apply to the infrared and ultraviolet wavelengths, as well as any other electromagnetic radiation for which the films are designed.

Absorbance is another consideration. For most applications, it is advantageous for neither the first polymer nor the second polymer to have any absorbance bands within the bandwidth of interest for the film in question. Thus, all incident light within the bandwidth is either reflected or transmitted. However, for some applications, it may be useful for one or both of the first and second polymer to absorb specific wavelengths, either totally or in part.

Although many polymers may be chosen as the first polymer, certain of the polyesters have the capability for particularly large birefringence. Among these, polyethylene 2,6-naphthalate (PEN) is frequently chosen as a first polymer for films of the present invention. It has a very large positive stress optical coefficient, retains birefringence effectively after stretching, and has little or no absorbance within the visible range. It also has a large index of refraction in the isotropic state. Its refractive index for polarized incident light of 550 nm wavelength increases when the plane of polarization is parallel to the stretch direction from about 1.64 to as high as about 1.9. Its birefringence can be increased by increasing its molecular orientation which, in turn, may be increased by stretching to greater stretch ratios with other stretching conditions held fixed.

Other semicrystalline naphthalene dicarboxylic polyesters are also suitable as first polymers. Polybutylene 2,6-Naphthalate (PBN) is an example. These polymers may be homopolymers or copolymers, provided that the use of comonomers does not substantially impair the stress optical coefficient or retention of birefringence after stretching. The term "PEN" herein will be understood to include copolymers of PEN meeting these restrictions. In practice, these restrictions imposes an upper limit on the comonomer content, the exact value of which will vary with the choice of comonomer(s) employed. Some compromise in these properties may be accepted, however, if comonomer incorporation results in improvement of other properties. Such properties include but are not limited to improved interlayer adhesion, lower melting point (resulting in lower extrusion temperature), better rheological matching to other polymers in the film, and advantageous shifts in the process window for stretching due to change in the glass transition temperature.

Suitable comonomers for use in PEN, PBN or the like may be of the diol or dicarboxylic acid or ester type. Dicarboxylic acid comonomers include but are not limited to terephthalic acid, isophthalic acid, phthalic acid, all isomeric naphthalenedicarboxylic acids (2,6-, 1,2-, 1,3-, 1,4-, 1,5-, 1,6-, 1,7-, 1,8-, 2,3-, 2,4-, 2,5-, 2,7-, and 2,8-), bibenzoic acids such as 4,4'-biphenyl dicarboxylic acid and its isomers, trans-4,4'-stilbene dicarboxylic acid and its isomers, 4,4'-diphenyl ether dicarboxylic acid and its isomers, 4,4'-diphenylsulfone dicarboxylic acid and its isomers, 4,4'-benzophenone dicarboxylic acid and its isomers, halogenated aromatic dicarboxylic acids such as 2-chloroterephthalic acid and 2,5-dichloroterephthalic acid, other substituted aromatic dicarboxylic acids such as tertiary butyl isophthalic acid and sodium sulfonated isophthalic acid, cycloalkane dicarboxylic acids such as 1,4-cyclohexanedicarboxylic acid and its isomers and 2,6-decahydronaphthalene dicarboxylic acid and its isomers, bi- or multi-cyclic dicarboxylic acids (such as the various isomeric norbornane and norbornene dicarboxylic acids, adamantane dicarboxylic acids, and bicyclo-octane dicarboxylic acids), alkane dicarboxylic acids (such as sebacic acid, adipic acid, oxalic acid, malonic acid, succinic acid, glutaric acid, azelaic acid, and dodecane dicarboxylic acid.), and any of the isomeric dicarboxylic acids of the fused-ring aromatic hydrocarbons (such as indene, anthracene, pheneanthrene, benzonaphthene, fluorene and the like). Alternatively, alkyl esters of these monomers, such as dimethyl terephthalate, may be used.

Suitable diol comonomers include but are not limited to linear or branched alkane diols or glycols (such as ethylene glycol, propanediols such as trimethylene glycol, butanediols such as tetramethylene glycol, pentanediols such as neopentyl glycol, hexanediols, 2,2,4-trimethyl-1,3-pentanediol and higher diols), ether glycols (such as diethylene glycol, triethylene glycol, and polyethylene glycol), chain-ester diols such as 3-hydroxy-2,2-dimethylpropyl-3-hydroxy-2,2-dimethyl propanoate, cycloalkane glycols such as 1,4-cyclohexanedimethanol and its isomers and 1,4-cyclohexanediol and its isomers, bi- or multicyclic diols (such as the various isomeric tricyclodecane dimethanols, norbornane dimethanols, norbornene dimethanols, and bicyclo-octane dimethanols), aromatic glycols (such as 1,4-benzenedimethanol and its isomers, 1,4-benzenediol and its isomers, bisphenols such as bisphenol A, 2,2'-dihydroxy biphenyl and its isomers, 4,4'-dihydroxymethyl biphenyl and its isomers, and 1,3-bis(2-hydroxyethoxy)benzene and its isomers), and lower alkyl ethers or diethers of these diols, such as dimethyl or diethyl diols.

Tri- or polyfunctional comonomers, which can serve to impart a branched structure to the polyester molecules, can also be used. They may be of either the carboxylic acid, ester, hydroxy or ether types. Examples include, but are not limited to, trimellitic acid and its esters, trimethylol propane, and pentaerythritol.

Also suitable as comonomers are monomers of mixed functionality, including hydroxycarboxylic acids such as parahydroxybenzoic acid and 6-hydroxy-2-naphthalenecarboxylic acid, and their isomers, and tri- or polyfunctional comonomers of mixed functionality such as 5-hydroxyisophthalic acid and the like.

Polyethylene terephthalate (PET) is another material that exhibits a significant positive stress optical coefficient, retains birefringence effectively after stretching, and has little or no absorbance within the visible range. Thus, it and its high PET-content copolymers employing comonomers listed above may also be used as first polymers in some applications of the current invention. The term "PET" as used herein will be understood to include PET and its high PET content copolymers that function similarly to PET alone.

When a naphthalene dicarboxylic polyester such as PEN or PBN is chosen as first polymer, there are several approaches which may be taken to the selection of a second polymer. One preferred approach for some applications is to select a naphthalene dicarboxylic copolyester (coPEN) formulated so as to develop significantly less or no birefringence when stretched. This can be accomplished by choosing comonomers and their concentrations in the copolymer such that crystallizability of the coPEN is eliminated or greatly reduced. One typical formulation employs as the dicarboxylic acid or ester components dimethyl naphthalate at from about 20 mole percent to about 80 mole percent and dimethyl terephthalate or dimethyl isophthalate at from about 20 mole percent to about 80 mole percent, and employs ethylene glycol as diol component. Of course, the corresponding dicarboxylic acids may be used instead of the esters. The number of comonomers which can be employed in the formulation of a coPEN second polymer is not limited. Suitable comonomers for a coPEN second polymer include but are not limited to all of the comonomers listed above as suitable PEN comonomers, including the acid, ester, hydroxy, ether, tri- or polyfunctional, and mixed functionality types.

Often it is useful to predict the isotropic refractive index of a coPEN second polymer. A volume average of the refractive indices of the monomers to be employed has been found to be a suitable guide. Similar techniques well-known in the art can be used to estimate glass transition temperatures for coPEN second polymers from the glass transitions of the homopolymers of the monomers to be employed.

In addition, polycarbonates having a glass transition temperature compatible with that of PEN and having a refractive index similar to the isotropic refractive index of PEN are also useful as second polymers. Polyesters, copolyesters, polycarbonates, and copolycarbonates may also be fed together to an extruder and transesterified into new suitable copolymeric second polymers.

It is not required that the second polymer be a copolyester or copolycarbonate. Vinyl polymers and copolymers made from monomers such as vinyl naphthalenes, styrenes, ethylene, maleic anhydride, acrylates, acetates, and methacrylates may be employed. Condensation polymers other than polyesters and polycarbonates may also be used. Examples include: polysulfones, polyamides, polyurethanes, polyamic acids, and polyimides. Naphthalene groups and halogens such as chlorine, bromine and iodine are useful for increasing the refractive index of the second polymer to a desired level. Acrylate groups and fluorine are particularly useful in decreasing refractive index when this is desired.

It will be understood from the foregoing discussion that the choice of a second polymer is dependent not only on the intended application of the multilayer optical film in question, but also on the choice made for the first polymer, and the processing conditions employed in stretching. Suitable second polymer materials include but are not limited to polyethylene naphthalate (PEN) and isomers thereof (such as 2,6-, 1,4-, 1,5-, 2,7-, and 2,3-PEN), polyalkylene terephthalates (such as polyethylene terephthalate, polybutylene terephthalate, and poly-1,4-cyclohexanedimethylene terephthalate), other polyesters, polycarbonates, polyarylates, polyamides (such as nylon 6, nylon 11, nylon 12, nylon 4/6, nylon 6/6, nylon 6/9, nylon 6/10, nylon 6/12, and nylon 6/T), polyimides (including thermoplastic polyimides and polyacrylic imides), polyamide-imides, polyether-amides, polyetherimides, polyaryl ethers (such as polyphenylene ether and the ring-substituted polyphenylene oxides), polyarylether ketones such as polyetheretherketone ("PEEK"), aliphatic polyketones (such as copolymers and terpolymers of ethylene and/or propylene with carbon dioxide), polyphenylene sulfide, polysulfones (including polyethersulfones and polyaryl sulfones), atactic polystyrene, syndiotactic polystyrene ("sPS") and its derivatives (such as syndiotactic poly-alpha-methyl styrene and syndiotactic polydichlorostyrene), blends of any of these polystyrenes (with each other or with other polymers, such as polyphenylene oxides), copolymers of any of these polystyrenes (such as styrene-butadiene copolymers, styrene-acrylonitrile copolymers, and acrylonitrile-butadiene-styrene terpolymers), polyacrylates (such as polymethyl acrylate, polyethyl acrylate, and polybutyl acrylate), polymethacrylates (such as polymethyl methacrylate, polyethyl methacrylate, polypropyl methacrylate, and polyisobutyl methacrylate), cellulose derivatives (such as ethyl cellulose, cellulose acetate, cellulose propionate, cellulose acetate butyrate, and cellulose nitrate), polyalkylene polymers (such as polyethylene, polypropylene, polybutylene, polyisobutylene, and poly(4-methyl)pentene), fluorinated polymers and copolymers (such as polytetrafluoroethylene, polytrifluoroethylene, polyvinylidene fluoride, polyvinyl fluoride, fluorinated ethylene-propylene copolymers, perfluoroalkoxy resins, polychlorotrifluoroethylene, polyethylene-co-trifluoroethylene, polyethylene-co-chlorotrifluoroethylene), chlorinated polymers (such as polyvinylidene chloride and polyvinyl chloride), polyacrylonitrile, polyvinylacetate, polyethers (such as polyoxymethylene and polyethylene oxide), ionomeric resins, elastomers (such as polybutadiene, polyisoprene, and neoprene), silicone resins, epoxy resins, and polyurethanes.

Also suitable are copolymers, such as the copolymers of PEN discussed above as well as any other non- naphthalene group -containing copolyesters which may be formulated from the above lists of suitable polyester comonomers for PEN. In some applications, especially when PET serves as the first polymer, copolyesters based on PET and comonomers from said lists above (coPETs) are especially suitable. In addition, either first or second polymers may consist of miscible or immiscible blends of two or more of the above-described polymers or copolymers (such as blends of sPS and atactic polystyrene, or of PEN and sPS). The coPENs and coPETs described may be synthesized directly, or may be formulated as a blend of pellets where at least one component is a polymer based on naphthalene dicarboxylic acid or terephthalic acid and other components are polycarbonates or other polyesters, such as a PET, a PEN, a coPET, or a co-PEN.

Another preferred family of materials for the second polymer for some applications are the syndiotactic vinyl aromatic polymers, such as syndiotactic polystyrene. Syndiotactic vinyl aromatic polymers useful in the current invention include poly(styrene), poly(alkyl styrene)s, poly (aryl styrene)s, poly(styrene halide)s, poly(alkoxy styrene)s, poly(vinyl ester benzoate), poly(vinyl naphthalene), poly (vinylstyrene), and poly(acenaphthalene), as well as the hydrogenated polymers and mixtures or copolymers containing these structural units. Examples of poly(alkyl styrene)s include the isomers of the following: poly(methyl styrene), poly(ethyl styrene), poly(propyl styrene), and poly (butyl styrene). Examples of poly(aryl styrene)s include the isomers of poly(phenyl styrene). As for the poly(styrene halide)s, examples include the isomers of the following: poly(chlorostyrene), poly(bromostyrene), and poly (fluorostyrene). Examples of poly(alkoxy styrene)s include the isomers of the following: poly(methoxy styrene) and poly(ethoxy styrene). Among these examples, particularly preferable styrene group polymers, are: polystyrene, poly (p-methyl styrene), poly(m-methyl styrene), poly(p-tertiary butyl styrene), poly(p-chlorostyrene), poly(m-chloro styrene), poly(p-fluoro styrene), and copolymers of styrene and p-methyl styrene.

Furthermore, comonomers may be used to make syndiotactic vinyl aromatic group copolymers. In addition to the monomers for the homopolymers listed above in defining the syndiotactic vinyl aromatic polymers group, suitable comonomers include olefin monomers (such as ethylene, propylene, butenes, pentenes, hexenes, octenes or decenes), diene monomers (such as butadiene and isoprene), and polar vinyl monomers (such as cyclic diene monomers, methyl methacrylate, maleic acid anhydride, or acrylonitrile).

The syndiotactic vinyl aromatic copolymers of the present invention may be block copolymers, random copolymers, or alternating copolymers.

The syndiotactic vinyl aromatic polymers and copolymers referred to in this invention generally have syndiotacticity of higher than 75% or more, as determined by carbon-13 nuclear magnetic resonance. Preferably, the degree of syndiotacticity is higher than 85% racemic diad, or higher than 30%, or more preferably, higher than 50%, racemic pentad.

In addition, although there are no particular restrictions regarding the molecular weight of these syndiotactic vinyl aromatic polymers and copolymers, preferably, the weight average molecular weight is greater than 10,000 and less than 1,000,000, and more preferably, greater than 50,000 and less than 800,000.

The syndiotactic vinyl aromatic polymers and copolymers may also be used in the form of polymer blends with, for instance, vinyl aromatic group polymers with atactic structures, vinyl aromatic group polymers with isotactic structures, and any other polymers that are miscible with the vinyl aromatic polymers. For example, polyphenylene ethers show good miscibility with many of the previous described vinyl aromatic group polymers.

When a polarizing film is made using a process with predominantly uniaxial stretching, particularly preferred combinations of polymers for optical layers include PEN/coPEN, PET/coPET, PEN/sPS, PET/sPS, PEN/Eastar,™ and PET/Eastar,™ where "coPEN" refers to a copolymer or blend based upon naphthalene dicarboxylic acid (as described above) and Eastar™ is a polyester or copolyester (believed to comprise cyclohexanedimethylene diol units and terephthalate units) commercially available from Eastman Chemical Co. When a polarizing film is to be made by manipulating the process conditions of a biaxial stretching process, particularly preferred combinations of polymers for optical layers include PEN/coPEN, PEN/PET, PEN/PBT, PEN/PETG and PEN/PETcoPBT, where "PBT" refers to polybutylene terephthalate, "PETG" refers to a copolymer of PET employing a second glycol (usually cyclohexanedimethanol), and "PETcoPBT" refers to a copolyester of terephthalic acid or an ester thereof with a mixture of ethylene glycol and 1,4-butanediol.

Particularly preferred combinations of polymers for optical layers in the case of mirrors or colored films include PEN/PMMA, PET/PMMA, PEN/Ecdel,™ PET/Ecdel,™ PEN/sPS, PET/sPS, PEN/coPET, PEN/PETG, and PEN/THV,™ where "PMMA" refers to polymethyl methacrylate, Ecdel™ is a thermoplastic polyester or copolyester (believed to comprise cyclohexanedicarboxylate units, polytetramethylene ether glycol units, and cyclohexanedimethanol units) commercially available from Eastman Chemical Co., "coPET" refers to a copolymer or blend based upon terephthalic acid (as described above), "PETG" refers to a copolymer of PET employing a second glycol (usually cyclohexanedimethanol), and THV™ is a fluoropolymer commercially available from 3M Co.

For mirror films, a match of the refractive indices of the first polymer and second polymer in the direction normal to the film plane is sometimes preferred, because it provides for constant reflectance with respect to the angle of incident light (that is, there is no Brewster's angle). For example, at a specific wavelength, the in-plane refractive indices might be 1.76 for biaxially oriented PEN, while the film plane-normal refractive index might fall to 1.49. When PMMA is used as the second polymer in the multilayer construction, its refractive index at the same wavelength, in all three directions, might be 1.495. Another example is the PET/Ecdel™ system, in which the analogous indices might be 1.66 and 1.51 for PET, while the isotropic index of Ecdel™ might be 1.52.

It is sometimes preferred for the multilayer optical films of the current invention to consist of more than two distinguishable polymers. A third or subsequent polymer might be fruitfully employed as an adhesion-promoting layer between the first polymer and the second polymer within an optical stack, as an additional component in a stack for optical purposes, as a protective boundary layer between optical stacks, as a skin layer, as a functional coating, or for any other purpose. As such, the composition of a third or subsequent polymer, if any, is not limited. Some preferred multicomponent constructions are described in U.S. patent application Ser. No. 09/006,118 (filed Jan. 13, 1998).

The selection criteria for the materials of the optical stack layers may also be useful in the selection of appropriate materials for thick internal or external skin protective layers. The criteria for the second polymer may be more desirable than those for the first polymer. In some cases, however, the mechanical properties of the birefringent first material, such as high glass transition temperature to reduce sticking to rollers, low coefficients of thermal expansion, mechanical stiffness, etc., may be desirable. In the case of films designed for post-forming, it may be desirable to use materials of lower draw stiffness to improve formability at a given applied stress, e.g., vacuum pressure, or otherwise improve extensibility.

EXAMPLES

Advantages of the invention are illustrated by the following examples. However, the particular materials and amounts thereof recited in these examples, as well as other conditions and details, are to be interpreted to apply broadly in the art and should not be construed to unduly limit the invention.

Example 1

Example 1 illustrates the use of the multilayer optical film for use as a light guide for dental photo-curing lights. The optical film was rolled into a tube of similar diameter to the lighting end of the Visilux 2™ (3M, St. Paul) dental curing light. The tube was secured with adhesive and placed in flush contact with the external surface of the lighting end of the Visilux 2™. The light output was measured using a Cure Rite visible light meter (Efos Inc., Model 8000) at 120 seconds. As the Visilux 2™ is moved a measured distance away from the surface, the light output dropped significantly as shown in examples C1.2 and C1.3. As shown in example C1.3, at an approximate distance of 4 inches away, the light intensity was very low. In contrast, as shown in Example 1.4, the light intensity at 1 inch was much higher with the multilayer optical film light tube. Even at a distance of 4 inches, Example 1.5, the light intensity as measured by the meter was adequate.

TABLE 1

| Example | Light Multilayer Light Tube | Distance (in) | Light Output (mW/cm$^2$) |
| --- | --- | --- | --- |
| C1.1 | None | 0 | 472.0 |
| C1.2 | None | 1 | 116.5 |
| C1.3 | None | 4 | 12.5 |
| 1.4 | Yes | 1 | 328.0 |
| 1.5 | Yes | 4 | 203.0 |

Example 2

Example 2 illustrates that the multilayer optical film has a unique ability to act as a UV filter due the presence of a UV absorbing polymer such as PEN. The UV output was measured by placing the tip of the Visilux 2™ dental photo-curing light on the reading surface of a Dynachem UV Integrating Radiometer (Sterling Va.) for 10 seconds. As shown in Table 2, the UV light output of the curing light, which performed within the requirements for dental curing lights, was nonetheless significantly higher in the absence of the UV filter. The efficiency of the filter could be increased by a thicker film or optimizing UV absorbing components in the multilayer optical film. The film based UV multilayer optical film filter could be used to reduce the overall weight of a photo-curing light.

TABLE 2

| Example | Optical Filter | Dynachem UV Output (Joules/cm$^2$) |
| --- | --- | --- |
| C2.1 | None | 676.0 |
| 2.2 | One film layer | 485.0 |

Example 3

Example 3 is a trifurcated light guide was vacuum formed from a highly reflective PEN/PMMA multilayer mirror film that was made as described in Example 2 of U.S. patent application Ser. No. 08/494,366. A coextruded film containing 601 layers was made on a sequential flat-film-making line via a coextrusion process. Polyethylene Naphthalate (PEN) with an Intrinsic Viscosity of 0.57 dl/g (60 wt. % phenol/40 wt. % dichlorobenzene) was delivered by extruder A at a rate of 114 pounds per hour with 64 pounds per hour going to the feedblock and the rest going to skin layers described below. PMMA (CP-82 from ICI of Americas) was delivered by extruder B at a rate of 61 pounds per hour with all of it going to the feedblock. PEN was on the skin layers of the feedblock. The feedblock method was used to generate 151 layers using the feedblock such as those described in U.S. Pat. No. 3,801,429, after the feedblock two symmetric skin layers were coextruded using extruder C metering about 30 pounds per hour of the same type of PEN delivered by extruder A. This extrudate passed through two multipliers producing an extrudate of about 601 layers. U.S. Pat. No. 3,565,985 describes similar coextrusion multipliers. The extrudate passed through another device that coextruded skin layers at a total rate of 50 pounds per hour of PEN from extruder A. The web was length oriented to a draw ratio of about 3.2 with the web temperature at about 280° F. The film was subsequently preheated to about 310° F. in about 38 seconds and drawn in the transverse direction to a draw ratio of about 4.5 at a rate of about 11% per second. The film was then heat-set at 440° F. with no relaxation allowed. The finished film thickness was about 3 mil. The bandwidth at normal incidence was about 350 nm with an average in-band extinction of greater than 99%. The amount of optical absorption was difficult to measure because of its low value, but was less than 1%.

A 17.8 cm (7 inch) by 25.4 cm (10 inch) by 2.5 cm (1 inch) block of wood was used to prepare a vacuum forming mold. A series of small holes were drilled in the lowest part of grooves routed in the wood as generally illustrated in FIG. 13C. After removing the release liner from one side of an acrylic foam double sided tape, the adhesive was applied to the periphery on the non-routed side of the wood block to form a chamber beneath the mold; the second release liner was not removed from the other side of the adhesive tape. The mold was then placed on the vacuum table of a vacuum forming apparatus. The multilayer film was mounted in a heating frame, and the film was heated for 4 minutes beneath an electrical heating element to 177° C. (350° C.). The film was then rapidly lowered onto the evacuated mold, drawing the polymer film into the grooved cavity. The film maintained its high reflectivity after the vacuum forming operation.

While the formed film was still in the mold, double-sided adhesive tape was applied to the portions of the film that were not drawn into the mold. A second sheet of mirror film was then adhered to the formed mirror film. The tips of the four termini were cut off to form an inlet with three outlets as shown in FIG. 13C. The terminus of a fiber optic light fixture was inserted into the inlet of the light guide, and when light was directed into the light guide input, light emerged from each of the outlets.

A sample of the multilayer mirror film (PEN/PMMA) was rolled into a tube approximately 4 inches long and ¼" in diameter. The tube was inserted into a 3M Visilux 2™ dental curing light. The curing light was energized, and the light was effectively transported through the light guide.

A comparison of three reflective films for light reflectivity are presented in Table 3. Silver-Lux™ film, 90/50 Brightness Enhancement Film II™ (BEF), and multilayer mirror film were cut into 4"×18" strips. The Silver-Lux™ and multilayer mirror film were rolled into tubes and inserted in 16" long sections of grey PVC pipe (¼" thick wall, 1" internal diameter). The 90/50 Brightness Enhancement Film II™ was rolled into a tube with the grooves to the outside of the tube running parallel with the tube's long axis. The 90/50 Brightness Enhancement Film II™ was then inserted into a section of the grey PVC pipe. Each light guide was evaluated for its ability to transport light. A Newport tungsten-halogen stabilized 780 lamp was inserted into one end of the light guide, and the other end of the light guide was inserted into a 6" diameter Labsphere integrating sphere. The light was measured using a Graseby/Optronic light meter.

TABLE 3

| Film Light Tube | Measurement Candela/m² | Relative Power |
| --- | --- | --- |
| Silver-Lux | 125 | 0.80 |
| 90/50 BEF II | 119 | 0.76 |
| Multilayer Mirror | 135 | 0.87 |
| Total Light | 156 | 1.00 |

The patents, patent documents, and publications cited herein are incorporated by reference in their entirety, as if each were individually incorporated by reference. Various modifications and alterations of this invention will become apparent to those skilled in the art without departing from the scope of this invention, and it should be understood that this invention is not to be unduly limited to the illustrative embodiments set forth herein.

What is claimed is:

1. A dental article comprising at least one optical surface reflecting light of desired wavelengths, wherein the optical surface comprises a post-formed optical stack comprising a plurality of layers, the layers comprising at least one birefringent polymer and at least one different polymer, wherein the optical stack comprises first and second strain-induced index of refraction differentials, the first and second index of refraction differentials being located along first and second perpendicular in-plane axes, and further wherein the thickness of the post-formed optical stack varies over the optical surface.

2. A dental article according to claim 1, wherein substantially the entire optical stack reflects at least about 85% of light of the desired wavelengths.

3. A dental article according to claim 1, wherein the thickness of the optical stack varies by at least about 10% or more.

4. A dental article according to claim 1, wherein the article comprises a dental implement.

5. A dental article according to claim 4, further comprising an anti-fog coating on the optical surface.

6. A dental article according to claim 4, wherein the optical surface is removably attached to the dental implement.

7. A dental article according to claim 4, wherein the dental implement comprises a dental mirror including a handle and a head connected to the handle, wherein the optical surface is located on the head of the mirror.

8. A dental article according to claim 7, wherein the optical surface is convex.

9. A dental article according to claim 7, wherein the optical surface is removably attached to the head.

10. A dental article according to claim 9, wherein the head further comprises at least one retaining element, and further wherein the optical surface is retained in place on the head by the at least one retaining element.

11. A dental article according to claim 10, wherein the retaining element comprises a clamp.

12. A dental article according to claim 10, wherein the retaining element comprises adhesive.

13. A dental article according to claim 4, wherein the dental implement comprises a light guide for use in connection with photo-curing dental restorative material, the light guide comprising a tubular body having first and second ends, the first end adapted for attachment to a light source, wherein the optical surface is located on the interior of the body.

14. A dental article according to claim 13, wherein the body tapers from the first end to the second end.

15. A dental article according to claim 13, wherein the desired wavelengths reflected by the optical surface are in the range of from about 420 nanometers to about 500 nanometers.

16. A dental article according to claim 4, wherein the dental implement comprises a matrix band including the optical surface.

17. A dental article according to claim 16, wherein the desired wavelengths reflected by the optical surface are in the range of from about 420 nanometers to about 500 nanometers.

18. A dental article according to claim 16, wherein a first portion of the optical surface transmits light of the desired wavelengths and a second portion of the optical surface reflects light of the desired wavelengths.

19. A dental article according to claim 1, wherein post-formed optical stack thickness varies non-uniformly.

20. A dental article according to claim 1, wherein the variations in thickness of the optical stack are greater than those found in the optical stack as manufactured.

21. A dental article according to claim 1, wherein the thickness of the optical stack varies by at least about 10% or more, and further wherein substantially the entire optical stack reflects at least about 85% of light of the desired wavelengths.

22. A dental article according to claim 1, wherein the optical surface is concave.

23. A dental article comprising:
   a lamp cavity comprising a first optical surface, the first optical surface reflecting light in a first set of desired wavelengths, the lamp cavity further comprising an opening; and
   a lens located over at least a portion of the opening in the lamp cavity, the lens comprising a second optical surface, wherein the second optical surface reflects light in a second set of desired wavelengths;
   wherein at least one of the first and second optical surfaces comprises an optical stack comprising a plurality of layers, the layers comprising at least one birefringent polymer and at least one different polymer, wherein the optical stack comprises first and second strain-induced index of refraction differentials, the first and second index of refraction differentials being located along first and second perpendicular in-plane axes, and further wherein the thickness of the optical stack varies over the optical surface.

24. A dental article according to claim 23, wherein the optical stack reflects at least about 90% of light of the desired wavelengths.

25. A dental article according to claim 23, wherein the first optical surface comprises the optical stack, and further wherein the first set of desired wavelengths reflected by the first optical surface does not include light in the range of from about 420 nanometers to about 500 nanometers.

26. A dental article according to claim 23, wherein the second set of desired wavelengths includes light in the range of from about 420 nanometers to about 500 nanometers.

27. A dental article according to claim 23, wherein the first optical surface comprises a first optical stack, ancd further wherein the first set of desired wavelengths reflected by the first optical surface does not include light in the range of from about 420 nanometers to about 500 nanometers, and still further wherein the second set of desired wavelengths includes light in the range of from about 420 nanometers to about 500 nanometers.

* * * * *

UNITED STATES PATENT AND TRADEMARK OFFICE
CERTIFICATE OF CORRECTION

PATENT NO. : 6,749,427 B1
DATED : June 15, 2004
INVENTOR(S) : Bretscher, Kathryn R.

It is certified that error appears in the above-identified patent and that said Letters Patent is hereby corrected as shown below:

Column 1,
Line 5, delete "articularly" and insert -- particularly --, therfor.
Line 6, delete "ultilayer" and insert -- multilayer --, therefor.

Column 3,
Line 20, delete "ultilayer" and insert -- multilayer --, therefor.

Column 6,
Line 15, delete "I0" and insert -- 10 --, therefor.

Column 7,
Line 23, delete "$\Delta z=0$" and insert -- $\Delta z \cong 0$ --, therefor.

Column 10,
Line 40, delete "he" and insert -- the --, therefor.

Column 11,
Line 9, delete "tf" and insert -- $t_f$ --, therefor.

Column 13,
Line 31, delete "t," and insert -- $t_1$ --, therefor.
Line 32, delete "12" and insert -- $t_2$ --, therefor.

Column 15,
Line 3, delete "comers" and insert -- corners --, therefor.

Column 18,
Line 13, delete "shapc" and insert -- shape --, therefor.

Column 23,
Line 23, delete "p" and insert -- $\rho$ --, therefor.

Column 26,
Line 32, delete "When" and insert -- when --, therefor.

UNITED STATES PATENT AND TRADEMARK OFFICE
CERTIFICATE OF CORRECTION

PATENT NO. : 6,749,427 B1
DATED : June 15, 2004
INVENTOR(S) : Bretscher, Kathryn R.

It is certified that error appears in the above-identified patent and that said Letters Patent is hereby corrected as shown below:

Column 28,
Line 58 and 60, delete "eak" and insert -- peak --, therefor.

Signed and Sealed this

Seventeenth Day of August, 2004

JON W. DUDAS
*Acting Director of the United States Patent and Trademark Office*